US009944784B2

(12) United States Patent
Woonton et al.

(10) Patent No.: US 9,944,784 B2
(45) Date of Patent: Apr. 17, 2018

(54) TEMPERATURE-RESPONSIVE POLYMER PARTICLES IN PROTEIN SEPARATION APPLICATIONS

(71) Applicants: COMMONWEALTH SCIENTIFIC AND INDUSTRIAL RESEARCH ORGANISATION, Australian Capital Territory (AU); MONASH UNIVERSITY, Victoria (AU)

(72) Inventors: Brad William Woonton, Victoria (AU); Milton Thomas William Hearn, Victoria (AU); Pankaj Maharjan, Victoria (AU); Kirthi De Silva, Victoria (AU); William Roy Jackson, Victoria (AU)

(73) Assignees: COMMONWEALTH SCIENTIFIC AND INDUSTRIAL RESEARCH ORGANISATION, Australian Capital Territory (AU); MONASH UNIVERSITY, Victoria (AU)

( * ) Notice: Subject to any disclaimer, the term of this patent is extended or adjusted under 35 U.S.C. 154(b) by 0 days.

(21) Appl. No.: 14/499,653

(22) Filed: Sep. 29, 2014

(65) Prior Publication Data
US 2015/0018440 A1 Jan. 15, 2015

Related U.S. Application Data

(62) Division of application No. 13/062,960, filed as application No. PCT/AU2009/001253 on Sep. 22, 2009, now Pat. No. 8,877,477.

(30) Foreign Application Priority Data

Sep. 22, 2008 (AU) ................................ 2008221604

(51) Int. Cl.
| | | |
|---|---|---|
| C08L 51/02 | (2006.01) |
| C08L 1/08 | (2006.01) |
| C08L 5/00 | (2006.01) |
| C08L 29/02 | (2006.01) |
| C08L 51/00 | (2006.01) |
| B01D 15/36 | (2006.01) |
| B01D 15/38 | (2006.01) |
| B01J 20/26 | (2006.01) |
| B01J 20/285 | (2006.01) |
| B01J 39/26 | (2006.01) |
| C07K 1/18 | (2006.01) |
| C08F 2/44 | (2006.01) |
| C08F 20/56 | (2006.01) |
| C08F 26/06 | (2006.01) |
| C08F 220/56 | (2006.01) |
| C08F 226/00 | (2006.01) |
| C08H 1/00 | (2006.01) |
| C08J 3/12 | (2006.01) |
| C08J 3/24 | (2006.01) |
| B01J 39/19 | (2017.01) |
| C08F 220/06 | (2006.01) |
| C08F 222/38 | (2006.01) |

(52) U.S. Cl.
CPC ............ *C08L 51/02* (2013.01); *B01D 15/362* (2013.01); *B01D 15/3876* (2013.01); *B01J 20/264* (2013.01); *B01J 20/267* (2013.01); *B01J 20/285* (2013.01); *B01J 39/19* (2017.01); *B01J 39/26* (2013.01); *C07K 1/18* (2013.01); *C08F 2/44* (2013.01); *C08F 20/56* (2013.01); *C08F 26/06* (2013.01); *C08F 220/56* (2013.01); *C08F 226/00* (2013.01); *C08H 1/00* (2013.01); *C08J 3/12* (2013.01); *C08J 3/24* (2013.01); *C08L 1/08* (2013.01); *C08L 5/00* (2013.01); *C08L 29/02* (2013.01); *C08L 51/003* (2013.01); *C08F 220/06* (2013.01); *C08F 222/385* (2013.01); *C08J 2333/26* (2013.01); *C08L 2555/80* (2013.01)

(58) Field of Classification Search
CPC ...... B01J 20/264; B01J 20/267; C08F 220/06; C08F 220/56; C08F 222/385; C08L 1/08; C08L 5/00; C08L 29/02; C08L 51/02; C08L 51/003
See application file for complete search history.

(56) References Cited

U.S. PATENT DOCUMENTS

| | | | | |
|---|---|---|---|---|
| 4,665,164 A | * | 5/1987 | Pernemalm | ......... C08B 37/0039 536/114 |
| 6,489,447 B1 | | 12/2002 | Basey et al. | |
| 2003/0205527 A1 | * | 11/2003 | Yoshizako | ............. B01D 15/20 210/656 |

(Continued)

FOREIGN PATENT DOCUMENTS

| | | |
|---|---|---|
| EP | 1 281 436 A1 | 2/2003 |
| WO | 99/57134 A1 | 11/1999 |
| WO | 01/74482 A1 | 10/2001 |

OTHER PUBLICATIONS

Sharma, B.K.; Chromatography, 2007, p. C-162.*

(Continued)

*Primary Examiner* — Robert Jones, Jr.
(74) *Attorney, Agent, or Firm* — Ladas & Parry LLP

(57) ABSTRACT

The present invention relates to a method for isolating proteins from a solution containing the proteins. The invention also relates to a method for the chromatographic separation of proteins. The present invention also relates to crosslinked hydroxylic polymer particles functionalized with temperature-responsive copolymer, and to methods of preparing such particles.

7 Claims, 12 Drawing Sheets

(56) References Cited

U.S. PATENT DOCUMENTS

2004/0134846 A1 7/2004 Akiyama et al.
2005/0063972 A1 3/2005 Basey et al.

OTHER PUBLICATIONS

Poole, C.F.; The Essence of Chromatography, 2003, p. 874-877.*
Forgacs, E., et al.; Molecular Basis of Chromatographic Separation, 1997, p. 120-121.*
Kobayashi, J. et al., "Cross-Linked Therrnoresponsive Anionic Polymer-Grafted Surfaces to Separate Bioactive Basic Peptides", Analytical Chemistry, vol. 75, No. 13, Jul. 1, 2003, pp. 3244-3249.
Sakamoto, C., et al, "Temperature- and pH-responsive aminopropyl-silica ion-exchange columns grafted with copolymers of N-isopropylacrylamide", Journal of Chromatography A, 2004, 1030, pp. 247-253.
Ayano, E., et al., "Aqueous chromatography system using temperature-responsive polymer-modified stationary phases", Journal of Separation Science, 2006, 29, pp. 738-749.
Hosoya, K., et al., "In Situ Surface-Selective Modification of Uniform Size Macroporous Polymer Particles with Temperature-Responsive Poly-N-isopropylacrylamide", Macromolecules, 1994, 27, pp. 3973-3976.
Adrados, B., et al., "Size exclusion behavior of hydroxypropylcellulose beads with temperature-dependent porosity", Journal of Chromatography A 2001, 930 (1-2), pp. 73-78.
Kanazawa, H., et al., "Temperature-Responsive Chromatographic Separation of Amino Acid Phenylthiohydantoins Using Aqueous Media as the Mobile Phase", Analytical Chemistry, 2000, 72, pp. 5961-5966.
Hoffman, A., et al., "Bioconjugates of Smart Polymers and Proteins: Synthesis and Applications", Macromolecular Symposia, 2004, 207, pp. 139-151.
Fundueanu, G., et al., "Preparation and characterization of pH- and temperature sensitive pullulan microspheres for controlled release of drugs", Biomaterials 29 (18), (Apr. 8, 2008), pp. 2767-2775.
Khan, A., "Preparation and characterizatiqn of N-isopropylacrylamide/acrylic acid copolymer core-shell microgel particles", Journal of Colloid and Interface Science, 313 (2), (2007), pp. 697-704.
Dowding, P., et al., "Preparation and Swelling Properties of Poly(NIPAM) "Minigel" Particles Prepared by Inverse Suspension Polymerization", Journal of Colloid and Interface Science, 221 (2), (2000), pp. 268-272.
Yu, H., et al., "Modified release of hydrophilic, hydrophobic and peptide agents from ionized amphiphilic gel networks", Journal of Controlled Release, 34 (2), (1995), pp. 117-127.
Maharjan, P., et al., "Novel chromatographic separation—The potential of smart polymers", Innovative Food Science & Emerging Technologies, 9 (2), (Apr. 2008), pp. 232-242.
Maharjan, P., et al., "Development of a temperature-responsive agarose-based ion-exchange chromatographic resin", Journal of Chromatography A, 1216, 2009, pp. 8722-8729.
Yin, X, et al., Temperature-Sensitive Hydrogel Microspheres Formed by Liquid-Liquid Phase Transitions of Aqueous Solutions of Poly(N,N-dimethylacrylamide-co-allyl methacrylate), Journal of Polymer Science: Part A: Polymer Chemistry, vol. 43, 2005 pp. 1641-1648.
Nagase, K., et al. "Preparation of Thermoresponsive Adsorption/ Elution Chromatography Matrices and Separation of Blood Proteins With Them"; Polymer Preprints, Japan, vol. 57, No. 2 2008 with English Abstract.
Kobayashi, J., et al., "Aqueous chromatography utilizing hydrophobicity-modified anionic temperature-responsive hydrogel for stationary phases", Journal of Chromatography A, 2002, 958, pp. 109-119.
Ayano, E., et al., "Aqueous chromatography system using pH- and temperature-responsive stationary phase with ion-exchange groups", Journal of Chromatography A, 2006, 1119, pp. 58-65.
Olivier, A., et al., "Surface-initiated controlled polymerization as a convenient method for designing functional polymer brushes: From self-assembled monolayers to patterned surfaces" , Progress in Polymer Science, vol. 37, 2012, pp. 157-181.
Carlmark, A., "Tailoring Cellulose Surfaces by Controlled Polymerization Methods", Macromolecular Chemistry and Physics, vol. 214, 2013, pp. 1539-1544.
Rajendran, P. B., et al., "Synthesis of Graft Copolymers onto Styrenic Polymer Backbone Via "Grafting From" RAFT Process", Journal of Polymer Science Part A: Polymer Chemistry, vol. 50, 2012, pp. 4772-4782.
Frauenrath, H., "Dendronized polymers—building a new bridge from molecules to nanoscopic objects", Prog. Polym. Sci., vol. 30, 2005, pp. 325-384.
Sarsabili, M, et al., "In Situ Reversible Addition—Fragmentation Chain Transfer Polymerization of Styrene in the Presence of MCM-41 Nanoparticles: Comparing "Grafting from" and "Grafting through" Approaches", Advances in Polymer Technology, vol. 32, No. 4, 2013, pp. 1-11.
Cai, T., et al., "Multi-functionalization of poly(vinylidene fluoride) membranes via combined "grafting from" and "grafting to" approaches", Soft Matter, vol. 7, 2011, pp. 11133-11143.

* cited by examiner

US 9,944,784 B2

TEMPERATURE-RESPONSIVE POLYMER PARTICLES IN PROTEIN SEPARATION APPLICATIONS

CROSS REFERENCE APPLICATIONS

This is a divisional of copending application Ser. No. 13/062,960 filed on Oct. 19, 2011, which is a 371 of International Application PCT/AU2009/001253 filed on Sep. 22, 2009, which designated the U.S., claims the benefit thereof and incorporates the same by reference. The non-provisional application designated above, namely application Ser. No. 13/062,960 filed Oct. 19, 2011, claims the benefit from Australian Patent Application 2008221604, the entire disclosure of which is incorporated herein by reference.

FIELD OF THE INVENTION

The present invention relates to a method for isolating proteins from a solution containing the proteins. The invention also relates to a method for the chromatographic separation of proteins. Further, the present invention also relates to crosslinked hydroxylic polymer particles functionalized with temperature-responsive copolymer, and to methods of preparing such particles.

BACKGROUND TO THE INVENTION

Chromatography is a technique employed to separate mixtures of molecules. It involves dissolving the mixture in a solvent or combination of solvents (a so-called mobile phase) to form a solution and subsequently passing the solution over a solid (the so-called stationary phase). The correct combination of mobile phase and stationary phase allow the molecules to be separated by permitting preferential or selective interaction of each molecule with the stationary phase to a differing extent. This differing interaction allows the molecules to be separated and thus isolated, analysed or identified. Both the chromatography mobile phase and the stationary phase are varied to suit (i) the type of molecules being separated, (ii) the scale of the separation (e.g. analytical, preparative or industrial), and (iii) the desired functionality of the separated molecules (e.g. bioactivity). Examples of mobile phases include acetonitrile, water, aqueous salt solution, methanol or mixtures thereof, while common stationary phases include ion-exchange, hydrophobic interaction or affinity interaction resins. Chromatography is employed extensively in the pharmaceutical and food industry for analytical purposes, and also to isolate valuable molecules at preparative and commercial scale.

'Smart' or 'intelligent' polymers are materials that undergo fast, reversible changes in their structure and function in response to external physical, chemical or electrical stimuli. Temperature is the most widely studied stimulus in 'smart polymer' systems and poly(N-isopropylacrylamide) (PolyNIPAAm) is a common and extensively studied temperature-responsive polymer.

Temperature-responsive materials have potential in on exchange chromatography as a versatile separation tool, where the elution of bound target bio-molecules can be induced by a mild physical change, such as an adjustment in temperature. These smart polymer chromatography systems offer promise in the cost-effective isolation of valuable components, particularly from agri-food, pharmaceutical, chemical and water and other complex feeds, in an environmentally-friendly manner.

PolyNIPAAm and related polymers have been used in the separations field to generate temperature-responsive stationary phases for ionic chromatography (Kobayashi et al., Analytical Chemistry, 2003, 75 (13), 3244-3249; Sakamoto at al, Journal of Chromatography A, 2004, 1030, 247-253; Ayano et al., Journal of Separation Science, 2006, 29, 738-749), size exclusion (Hosoya et al., Macromolecules, 1994, 27, 3973-3976; Adrados et al., Journal of Chromatography A 2001, 930 (1-2), 73-78), hydrophobic interaction (Kanazawa, et al., Analytical Chemistry, 2000, 72, 5961-5966), and affinity based chromatography separations (Hoffman and Stayton, Macromolecular Symposia, 2004, 207, 139-151) using a range of different supporting materials.

Further, a pH and temperature responsive copolymer of poly(N-isopropylacrylamide-co-acrylic acid-co-tert-butylacrylamide) grafted onto silica beads has been evaluated as an anionic temperature responsive chromatography medium (Kobayashi et al., Journal of Chromatography A, 2002, 958, 109-119; Kobayashi et al. Analytical Chemistry, 2003, 75 (13), 3244-3249). Effective separation of basic bioactive peptides under exclusively aqueous conditions was attained using anionic temperature/pH responsive polymer-modified surfaces. Similarly, silica beads grafted with poly(N-isopropylacrylamide-co-butyl methylacrylate-co-N,N'-dimethylaminopropylacrylamide) has been evaluated as a cationic temperature responsive chromatography medium (Sakamoto et al., Journal of Chromatography A, 2004, 1030, 247-253; Ayano et al., Journal of Chromatography A, 2006, 1119, 58-65). The medium was designed for efficient separation of bioactive compounds and pharmaceuticals using isocratic aqueous mobile phases.

There are a number of reports showing the use of smart polymers grafted onto silica beads for ion-exchange chromatography. However, the food and other industries tend to avoid silica base matrices due to cost, instability at the high pH and lack of operational robustness under the conditions often used in the food and other industries to clean equipment. In addition, silica based sorbents are generally applicable to analytical separations and lack the flexibility required for process applications in the food and other industries.

Further, previous investigations into the potential of smart polymers in cation exchange chromatography with modified silica beads have only been undertaken using small compounds like amino acids and steroids. There has been little published literature examining the retention and release of large proteins of significance to the food, pharmaceutical, chemical or water industries (e.g. lactoferrin) using temperature responsive ion exchange chromatographic resins.

There is a need for smart polymeric ion exchange resins on non-silica matrices. Specifically, there is a need for smart polymeric ion-exchange media based on a matrix that is compatible with systems currently employed by the food, pharmaceutical and other industries (such as cross linked agarose). Further, there is a need for thermally responsive cation exchange agarose based chromatography resin for application in the isolation of large proteins of commercial importance within the food and other industries (such as lactoferrin).

The discussion of the background to the invention herein is included to explain the context of the invention. This is not to be taken as an admission that any of the material referred to was published, known or part of the common general knowledge as at the priority date of any of the claims.

Throughout the description and claims of the specification the word "comprise" and variations of the word, such as "comprising" and "comprises", is not intended to exclude other additives, components, integers or steps.

SUMMARY OF THE INVENTION

The present invention provides a method for isolating proteins from a solution containing the proteins, the method including:
(a) contacting the solution containing the proteins with crosslinked polymer particles functionalized with temperature-responsive copolymer, wherein the temperature-responsive copolymer includes a proportion of ionizable chemical groups and said contacting occurs at a temperature between 30° C. and 80° C. to facilitate retention of the proteins by the crosslinked polymer particles;
(b) replacing the solution containing the protein with a rinse solution;
(c) replacing the rinse solution with a release solution effective for releasing the proteins from the crosslinked polymer particles into the solution;
(d) isolating the release solution containing the protein.

Viewed from a further aspect, the present invention provides crosslinked hydroxylic polymer particles functionalized with temperature-responsive copolymer, wherein the temperature-responsive copolymer includes a proportion of ionizable chemical groups.

Viewed from a further aspect, the present invention provides crosslinked hydroxylic polymer particles functionalized with temperature-responsive copolymer, wherein the temperature-responsive copolymer includes:
(a) monomer units providing temperature-responsive properties to the copolymer; and
(b) monomer units providing ionizable chemical groups to the copolymer.

Viewed from still a further aspect, the present invention provides a method for isolating proteins from a solution containing the proteins, the method including:
(a) contacting the solution containing the proteins with crosslinked polymer particles functionalized with temperature-responsive copolymer, wherein the temperature-responsive copolymer includes a proportion of ionizable chemical groups and said contacting occurs at a temperature between 30° C. and 80° C. to facilitate retention of the proteins by the crosslinked polymer particles;
(b) replacing the solution containing the protein with a rinse solution;
(c) replacing the rinse solution with a release solution effective for releasing the proteins from the crosslinked polymer particles into the solution; and
(d) isolating the release solution containing the protein.
wherein steps (a)-(c) occur in a chromatographic column having an inlet and an outlet.

Viewed from another aspect, the present invention provides a method for preparing crosslinked hydroxylic polymer particles functionalized with temperature-responsive copolymer having a proportion of ionizable chemical groups, the method including:
(a) providing crosslinked hydroxylic polymer particles;
(b) chemically modifying the crosslinked hydroxylic polymer particles to provide crosslinked hydroxylic polymer particles having functional groups capable of initiating polymerization;
(c) contacting the crosslinked hydroxylic polymer particles having functional groups capable of initiating polymerization with a monomer solution including at least one monomer capable of providing temperature-responsive properties to the copolymer and at least one monomer capable of providing ionizable chemical groups to the copolymer, wherein said contacting initiates polymerization of the monomers; and
(d) isolating crosslinked hydroxylic polymer particles functionalized with temperature-responsive copolymer having a proportion of ionizable chemical groups.

DETAILED DESCRIPTION OF THE INVENTION

Figure 1:
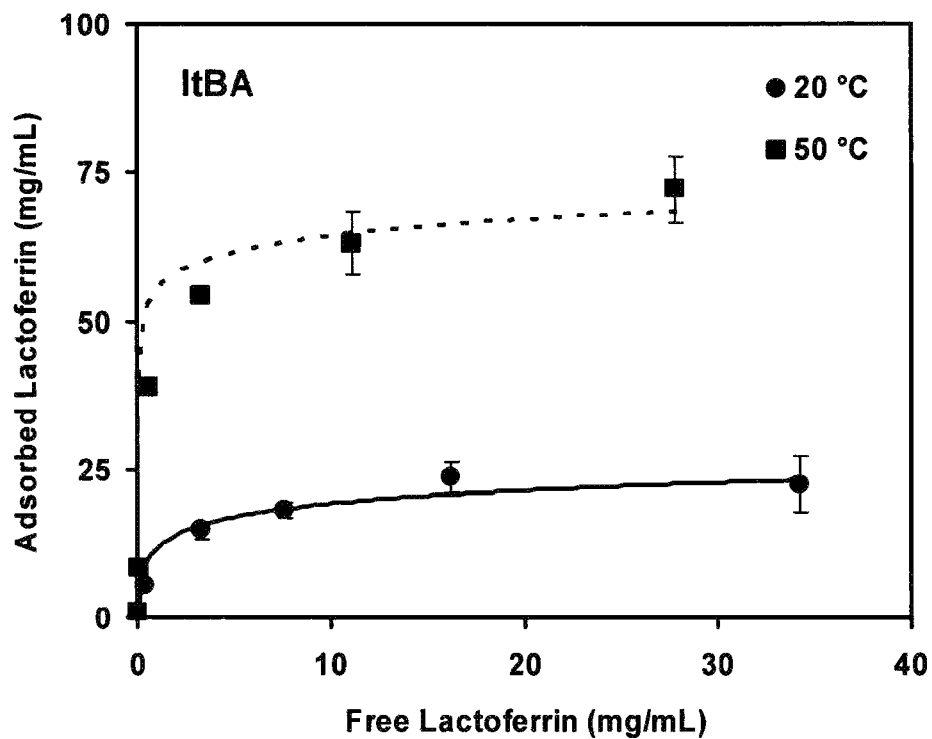
FIG. 1 shows lactoferrin adsorption isotherms for poly (N-isopropylacrylamide-co-tert-butylacrylamide-co-acrylic acid)-functionalized agarose (ItBA) and carboxymethyl functionalized agarose (CM) at 20° C. and 50° C., respectively.
Figure 1:
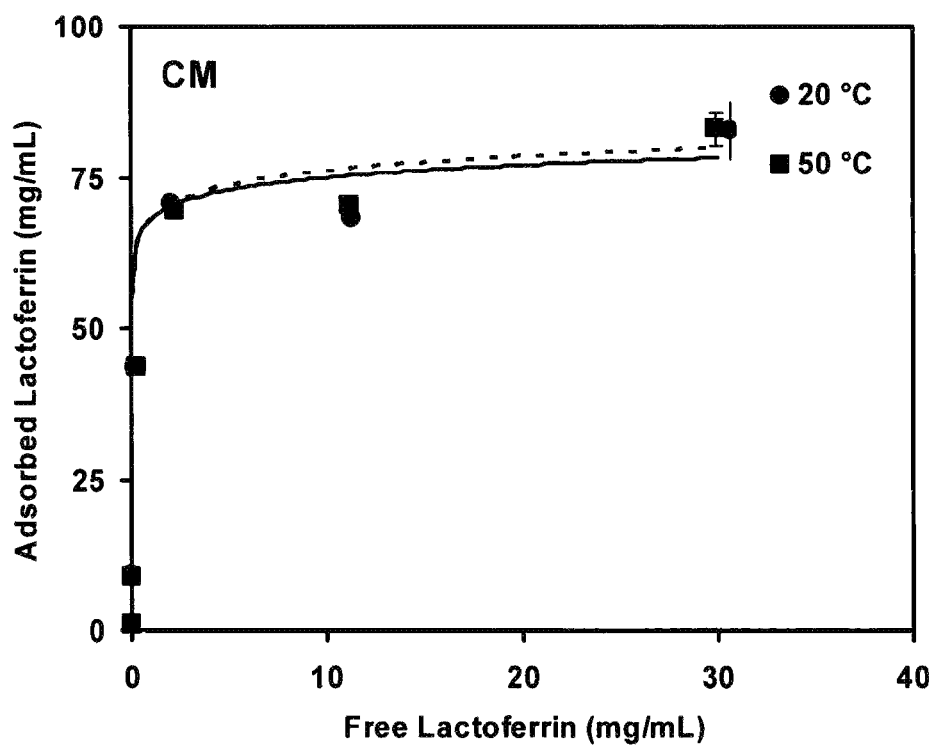

"Proteins" as defined herein are organic compounds made of amino acids arranged in a linear chain and joined together by peptide bonds between the carboxyl and amino groups of adjacent amino acid residues. Proteins are typically formed from the twenty standard amino acids, but may include other variants such as selenocysteine and pyrrolysine, or other synthetically produced chemical moieties. Proteins may be either single molecules or, alternatively, they may associate with one or more other proteins or molecules to form stable protein complexes. Proteins in the invention may be native, produced by genetic engineering methods and fermentation or cell culture or may have been chemically or physically modified. Proteins used in the invention may exist in one, two or multiple isoforms.

The term "protein solution" is taken to be any aqueous or non-aqueous liquid in which protein molecules are present. The protein solution may or may not include further biological molecules, solutes, co-solvents, buffers or additives. It may contain only one or more than one type of protein. The protein solution may be a product or by-product of another process, and may be a naturally occurring or synthetic liquid. Proteins in the protein solution may exist in single or in aggregated form. Whey solution and concentrated whey solution are examples of protein solutions.

"Temperature-responsive polymers" as defined herein are polymers having a lower critical solution temperature (LCST). The LCST of a polymer is the temperature at which a phase transition of the polymer solution occurs, typically being the temperature above which the polymer is no longer soluble in a particular solvent. Temperature-responsiveness can be manipulated by integration of hydrophobic or hydrophilic moieties into the polymer structure. The addition of hydrophobic or hydrophilic moieties into the structure can occur by post-synthesis modification of the temperature responsive polymer, or by use of a comonomer in the polymer synthesis which imparts either a proportion of hydrophilic groups or a proportion of hydrophobic groups. Copolymerization of a monomer giving rise to temperature responsive polymers with hydrophilic monomers leads to an increase in the polymer hydrophilicity and an increase in the LCST of the copolymer. By contrast, copolymerization of a monomer giving rise to temperature responsive polymers with hydrophobic monomers leads to an decrease in the polymer hydrophilicity and a decrease in the LCST of the copolymer. Typical monomers which are used to prepare temperature responsive polymers include N-isopropylacrylamide, vinyl methyl ether, N-vinylcaprolactam and N,N-diethylacrylamide. Examples of temperature responsive polymers include poly(N-isopropylacrylamide), poly(vinyl methyl ether).

The term "monomer" as defined herein is taken to be any chemical molecule from which can be formed a polymer containing a plurality of repeat units derived from the monomer. Monomers used in the present invention typically include those having an unsaturated group which can undergo polymerization by a radical, cationic or anionic mechanism. Monomers used in the invention are typically members of the acrylate, methacrylate, styrenic, acrylamide or methacrylamide families. Other monomers which may be suitable for use with the invention include monomers in the allylic and vinylic families. The term "monomer unit" is to be taken to be the repeat unit in a polymer or copolymer arising from the polymerization of the corresponding monomer.

The term "monomer capable of providing temperature-responsive properties to the copolymer" is taken to refer to any monomer known in the art as forming a temperature responsive polymer when polymerized, either when homo- or co-polymerized. Examples of monomers capable of providing temperature-responsive properties to the copolymer include N-isopropylacrylamide, vinyl methyl ether or N-vinylcaprolactam. In a specific embodiment the monomer capable of providing temperature-responsive properties is N-isopropylacrylamide. The term "monomer units providing temperature-responsive properties to the copolymer" is taken to refer to the monomer units in the copolymer which are derived from the monomer capable of providing temperature responsive properties to the copolymer.

The term "ionizable chemical groups" includes any chemical moiety which can give rise to a charged moiety. The species may become charged as a result of protonation (such as of an amine group to form an ammonium group), or by deprotonation (such as of a carboxylic acid or sulfonic acid group to form a carboxylate group or sulfonate group). Other ionizable chemical groups may be chemical groups which ionize in an aqueous environment, such as polymeric polysalts of alkali metal and alkali earth metal cations (such as sodium acrylate, calcium acrylate or lithium acrylate).

The term "monomer capable of providing ionizable chemical groups to the copolymer" includes any monomer, which, when incorporated into a polymer, provides chemical groups pendant to or on that polymer which are capable of becoming ionized and thereby providing a charged moiety on the polymer. Typical examples of monomer units providing ionizable chemical groups to the copolymer include acrylic acid, methacrylic acid, ethacrylic acid, sodium 2-acrylamido-2-methylpropanesulfonate, sodium 3-acrylamido-3-methylbutanoate, (3-acrylamidopropyl)trimethyl ammonium chloride, N,N-dimethylaminopropylacrylamide, N,N-dimethylaminoethyl methacrylate, N,N-dimethylaminoethyl acrylate, and 4-vinylbenzyltrimethylammonium chloride. In a specific embodiment the monomer providing ionizable chemical groups is acrylic acid. The term "monomer units providing ionizable chemical groups to the copolymer" refers to the units in the copolymer derived from the monomer capable of providing ionizable chemical groups to the copolymer.

"Bi-functional monomer" is taken to refer to monomers having two unsaturated groups each capable of participating in a polymerization reaction. Bi-functional monomers may, but need not be, symmetrical. Typical bi-functional monomers used in the invention include ethylene glycol dimethacrylate, 1,4-butanediol dimethacrylate, 1,6-hexanediol dimethacrylate, ethylene glycol diacrylate, 1,4-butanediol diacrylate, 1,6-hexanediol diacrylate, and N,N-methylenebisacrylamide. In a specific embodiment of the invention the bi-functional monomer is N,N-methylenebisacrylamide. The term bi-functional monomer unit is taken to refer to the repeat unit in a polymer or copolymer arising from the polymerization of the corresponding bi-functional monomer unit.

The "additional monomer unit(s)" is taken to be any additional monomer unit incorporated into the temperature-responsive copolymer. The additional monomer may be added to vary the hydrophilicity and/or hydrophobicity of the polymer, or to affect the charge density on the copolymer by diluting the monomer units providing ionizable groups to the copolymer. Typical examples of the additional monomer unit include methyl acrylate units, ethyl acrylate units, propyl acrylate units, butyl acrylate units, methyl methacrylate units, ethyl methacrylate units, propyl methacrylate units, N-isopropylmethacrylamide units, butyl methacrylate units, N-tert-butylacrylamide units, N,N-dimethylacrylamide units, N,N-diethylacrylamide units, and N-phenylacrylamide units. In a specific embodiment, the additional monomer units are N-tert-butylacrylamide units.

The term "chromatographic column" includes any glass, ceramic, metal or polymer cylinder through which the solution containing the protein to be separated is passed. The chromatographic column may house the plurality of crosslinked hydroxylic polymer particles functionalized with temperature-responsive polymer. The column may be part of an automated system through which the protein solution, rinse solution and release solution are pumped, or may be used manually as with gravity feed and a conventional tap. The column may be maintained at any specific temperature by housing the column inside an oven or temperature controlled bath, or by using any other heat exchange mechanism known in the art. The temperature controlled bath may be a temperature controlled water bath or a temperature controlled oil bath. The fluid used in the temperature bath may contain any other additive as would be appreciated by the person skilled in the art. The column may also have the temperature controlled by containing the column in a heat exchange jacket through which is passed a fluid of regulated temperature. The fluid may be liquid or gas. In some embodiments the fluid is liquid water. The column may have any dimensions (length, inner diameter, outer diameter) as deemed necessary for effective separation. The specific dimensions used will be evident to one having skill in the art.

The term "polymer particle" as used herein includes any particle formed principally from a carbon-based polymer. Polymer particles may include synthetic polymers such as those formed from polymerization of vinylic, allylic, acrylic, methacrylic, styrenic, acrylamido or methacrylamido monomers, or may include polysaccharide or cellulosic material. Polymer particles used in the invention may be hydrophilic or hydrophobic. Examples of polymer particles used in the invention include crosslinked agarose particles, crosslinked cellulose particles, hydrophilic crosslinked vinyl polymer particles, and methacrylate based polymeric resin particles. In some specific examples the crosslinked polymer particle is selected from the group consisting of Sepharose, Sephacel, Toyopearl, and Fractogel. In a specific embodiment of the invention, the crosslinked polymer particles are crosslinked agarose particles such as Sepharose particles.

The term "hydroxylic polymer particle" as used herein refers to any polymeric particle on which there is at least one hydroxyl group. Hydroxylic polymer particles may include hydroxyl-functionalized synthetic polymers such as those formed from polymerization of appropriate vinylic, allylic, acrylic, methacrylic, styrenic, acrylamido or methacrylamido monomers, or may include polysaccharide or cellulosic material. The hydroxyl functionality may be imparted to the polymer by polymerization of a monomer or comomoner having a hydroxyl functionality or having a precursor to a hydroxyl functionality which can be subsequently converted to a hydroxyl functionality. Alternatively the polymer may be modified post-polymerization by any chemical or physical means which can impart a hydroxyl functionality to the polymer. Hydroxylic polymer particles for use with the invention may be discrete particles or may be joined or fused together, or interconnected by bridges, so as to form a continuous network of hydroxylic polymer particles. In some embodiments of the invention the hydroxylic polymer particles may be joined, fused or interconnected together so as to form a so-called monolith. The connections between the particles in such a case may themselves be functionalized with temperature responsive polymer or may be unmodified polymeric material. Hydroxylic polymer particles used in the invention may be hydrophilic or hydrophobic. Examples of hydroxylic polymer particles used in the invention include crosslinked agarose particles, crosslinked cellulose particles, hydrophilic crosslinked vinyl polymer particles having hydroxyl groups, and methacrylate based polymeric resin particles having hydroxyl groups. In some specific examples the crosslinked polymer particle is selected from the group consisting of Sepharose, Sephacel, Toyopearl, and Fractogel. In a specific embodiment of the invention, the crosslinked polymer particles are crosslinked agarose particles such as Sepharose particles.

Throughout the specification and claims the term "polymerization" and derivatives thereof, such as "polymerize" and "polymerizing" is taken to mean any process of forming polymer molecules from monomer molecules. Polymerization refers not only to the situation where there is a single type of monomer, but also to situations in which there is more than one type of monomer leading to the formation of a so-called "copolymer". "Polymerization" is taken to include free radical polymerization, cationic polymerization and anionic polymerization. Polymerization is also taken to include those variants in which there are additional additives in the polymerization reaction, including atom transfer polymerization, atom transfer radical polymerization, catalytic chain transfer polymerization, chain transfer polymerization, group transfer polymerization, iodine mediated polymerization, nitroxide mediated polymerization, reversible addition fragmentation chain transfer polymerization, thioiniferter polymerization, iniferter polymerization, ring opening metathesis polymerization, acyclic diene metathesis polymerization and alternating diene metathesis polymerization.

"Functional groups capable of initiating polymerization" are taken to include any chemical moiety which can give rise to a species which is capable of initiating polymerization. In the case of free radical polymerization, atom transfer polymerization, atom transfer radical polymerization, catalytic chain transfer polymerization, chain transfer polymerization, group transfer polymerization, iodine mediated polymerization, nitroxide mediated polymerization, reversible addition fragmentation chain transfer polymerization, thioiniferter polymerization, iniferter polymerization, ring opening metathesis polymerization, acyclic diene metathesis polymerization and alternating diene metathesis polymerization, functional groups capable of initiating polymerization are those groups from which a radical can be formed. In some cases the formation of the radical occurs upon the elevation of the temperature. In other cases, the formation of the radical is triggered by the application of ultraviolet radiation. In still other cases the radical is formed by the application of ionizing radiation, such as gamma radiation or X-ray radiation.

The present invention provides batch and chromatographic methods for the separation of proteins. The present invention also provides crosslinked hydroxylic polymer particles functionalized with a temperature-responsive copolymer having a proportion of ionizable chemical groups, and methods of making the same.

From one aspect, the present invention provides a method for isolating proteins from a solution containing the proteins, the method including:
(a) contacting the solution containing the proteins with crosslinked polymer particles functionalized with temperature-responsive copolymer, wherein the temperature-responsive copolymer includes a proportion of ionizable chemical groups and said contacting occurs at a temperature between 30° C. and 80° C. to facilitate retention of the proteins by the crosslinked polymer particles;
(b) replacing the solution containing the protein with a rinse solution; and
(c) replacing the rinse solution with a release solution effective for releasing the proteins from the crosslinked polymer particles into the solution; and
(d) isolating the release solution containing the protein.

In some embodiments, the temperature of the release solution is lower than the temperature at which the solution containing the proteins was contacted with the crosslinked polymer particles. In some cases, the protein solution and the rinse solution are at a temperature between 30° C. and 60° C. In other cases, the protein solution and the rinse solution are at a temperature between 40° C. and 60° C. In some embodiments the release solution is at a temperature between 0° C. and 30° C. In other embodiments, the release solution is at a temperature between 0° C. and 20° C.

In some embodiments, the release solution contains an ionic solute. The ionic solute may be any ionic solute known in the art which is soluble in the release solution. In some preferred embodiments the ionic solute is an alkali metal halide or alkali earth metal halide. In a more preferred embodiment, the ionic solute is a lithium, sodium or potassium halide. In an even more preferred embodiment the ionic solute is lithium chloride, potassium chloride, sodium chloride, lithium bromide, potassium bromide, sodium bromide, lithium iodide, potassium iodide or sodium iodide. In some embodiments the ionic solute is selected from sodium chloride and potassium chloride. In some specific embodiments the ionic solute is sodium chloride.

In still a further embodiment of the invention the temperature-responsive copolymer includes:
(i) monomer units providing temperature-responsive properties to the copolymer; and
(ii) monomer units providing ionizable chemical groups to the copolymer.

In some embodiments, the monomer units providing temperature-responsive properties to the copolymer may be selected from the group consisting of N-isopropylacrylamide units, vinyl methyl ether units or N-vinylcaprolactam units. In a specific embodiment the monomer units providing temperature-responsive properties are N-isopropylacrylamide units.

Preferred examples of monomer units providing ionizable chemical groups may be selected from the group consisting of acrylic acid units, methacrylic acid units, ethacrylic acid units, sodium 2-acrylamido-2-methylpropanesulfonate units, sodium 3-acrylamido-3-methylbutanoate units, (3-acrylamidopropyl)trimethyl ammonium chloride units, N,N-dimethylaminopropylacrylamide units, N,N-dimethylaminoethyl methacrylate units, N,N-dimethylaminoethyl acrylate units, and 4-vinylbenzyltrimethylammonium chloride units. In a specific embodiment the monomer units providing ionizable chemical groups are acrylic acid units.

In a further embodiment of the invention, the temperature-responsive copolymer further includes at least one bi-functional monomer unit. The bi-functional monomer unit may be selected from the group consisting of ethylene glycol dimethacrylate units, 1,4-butanediol dimethacrylate units, 1,6-hexanediol dimethacrylate units, ethylene glycol diacrylate units, 1,4-butanediol diacrylate units, 1,6-hexanediol diacrylate units, and N,N-methylenebisacrylamide units. In a specific embodiment the bi-functional monomer unit are N,N-methylenebisacrylamide units.

In still another embodiment of the invention the temperature-responsive copolymer further includes at least one additional monomer unit. The additional monomer unit(s) may be selected from the group consisting of methyl acrylate units, ethyl acrylate units, propyl acrylate units, butyl acrylate units, methyl methacrylate units, ethyl methacrylate units, propyl methacrylate units, N-isopropylmethacrylamide units, butyl methacrylate units, N-tert-butylacrylamide units, N,N-dimethylacrylamide units, N,N-diethylacrylamide units, and N-phenylacrylamide units. In some specific embodiments, the additional monomer units are N-tert-butylacrylamide units. In other specific embodiments the additional monomer units are N-phenylacrylamide units.

In some embodiments of the invention the crosslinked polymer particles may be selected from the group consisting of crosslinked agarose particles, crosslinked cellulose particles, hydrophilic crosslinked vinyl polymer particles, and methacrylate based polymeric resin particles. In some embodiments of the invention the crosslinked polymer particle is selected from the group consisting of Sepharose, Sephacel, Toyopearl, and Fractogel. In a specific embodiment of the invention, the crosslinked polymer particles are crosslinked agarose particles such as Sepharose particles.

In some embodiments, the proteins are isolated from solution by a chromatographic method. Thus, a further aspect of the invention is to provide chromatographic methods for the separation of proteins.

From one aspect, the present invention provides a method for isolating proteins from a solution containing the proteins, the method including:
(a) contacting the solution containing the proteins with crosslinked polymer particles functionalized with temperature-responsive copolymer, wherein the temperature-responsive copolymer includes a proportion of ionizable chemical groups and said contacting occurs at a temperature between 30° C. and 80° C. to facilitate retention of the proteins by the crosslinked polymer particles;
(b) replacing the solution containing the protein with a rinse solution;
(c) replacing the rinse solution with a release solution effective for releasing the proteins from the crosslinked polymer particles into the solution; and
(d) isolating the release solution containing the protein. wherein steps (a)-(c) occur in a chromatographic column having an inlet and an outlet.

In some embodiments, the temperature of the release solution is lower than the temperature at which the solution containing the proteins was contacted with the crosslinked polymer particles. In some cases, the protein solution and the rinse solution are at a temperature between 30° C. and 60° C. In other cases, the protein solution and the rinse solution are at a temperature between 40° C. and 60° C. In some embodiments the release solution is at a temperature between 0° C. and 30° C. In other embodiments, the release solution is at a temperature between 0° C. and 20° C.

In some embodiments, the crosslinked polymer particles functionalized with temperature-responsive copolymer are included in the path between the inlet and outlet.

In some embodiments, the solution containing the proteins, the rinse solution and the release solution may be introduced sequentially through the inlet and collected from the outlet. In some embodiments, the product solution may be collected in discrete volumetric aliquots. In still other embodiments the concentration of protein in each aliquot is determined. In still a further embodiment, the concentration of the protein in the release solution is measured continuously.

In some embodiments, the release solution contains an ionic solute. The ionic solute may be any ionic solute known in the art which is soluble in the release solution. In some preferred embodiments the ionic solute is an alkali metal halide or alkali earth metal halide. In a more preferred embodiment, the ionic solute is a lithium, sodium or potassium halide. In an even more preferred embodiment the ionic solute is lithium chloride, potassium chloride, sodium chloride, lithium bromide, potassium bromide, sodium bromide, lithium iodide, potassium iodide or sodium iodide. In a some embodiments the ionic solute is sodium chloride or potassium chloride. In some specific embodiments the ionic solute is sodium chloride.

In some embodiments of the invention, the solution containing proteins, the rinse solution and the release solution are introduced to the chromatographic column by pumping. In other embodiments, the solution containing proteins, the rinse solution and the release solution are introduced by gravity.

In some embodiments of the invention the temperature-responsive copolymer includes:
(i) monomer units providing temperature-responsive properties to the copolymer; and
(ii) monomer units providing ionizable chemical groups to the copolymer.

The monomer units providing temperature-responsive properties to the copolymer may be selected from the group consisting of N-isopropylacrylamide units, vinyl methyl ether units or N-vinylcaprolactam units. In a specific embodiment the monomer units providing temperature-responsive properties are N-isopropylacrylamide units.

The monomer units providing ionizable chemical groups may be selected from the group consisting of acrylic acid units, methacrylic acid units, ethacrylic acid units, sodium 2-acrylamido-2-methylpropanesulfonate units, sodium 3-acrylamido-3-methylbutanoate units, (3-acrylamidopropyl)trimethyl ammonium chloride units, N,N-dimethylaminopropylacrylamide units, N,N-dimethylaminoethyl methacrylate units, N,N-dimethylaminoethyl acrylate units, and 4-vinylbenzyltrimethylammonium chloride units. In a specific embodiment the monomer units providing ionizable chemical groups are acrylic acid units.

In a further embodiment of the invention, the temperature-responsive copolymer further includes at least one bi-functional monomer unit. The bi-functional monomer unit may be selected from the group consisting of ethylene glycol dimethacrylate units, 1,4-butanediol dimethacrylate units, 1,6-hexanediol dimethacrylate units, ethylene glycol diacrylate units, 1,4-butanediol diacrylate units, 1,6-hexanediol diacrylate units, and N,N-methylenebisacrylamide units. In a specific embodiment the bi-functional monomer unit are N,N-methylenebisacrylamide units.

In still another embodiment of the invention the temperature-responsive copolymer further includes at least one additional monomer unit. The additional monomer unit(s) may be selected from the group consisting of methyl acrylate units, ethyl acrylate units, propyl acrylate units, butyl acrylate units, methyl methacrylate units, ethyl methacrylate units, propyl methacrylate units, N-isopropylmethacrylamide units, butyl methacrylate units, N-tert-butylacrylamide units, N,N-dimethylacrylamide units, N,N-diethylacrylamide units, and N-phenylacrylamide units. In some specific embodiments, the additional monomer units are N-tert-butylacrylamide units. In other specific embodiments the additional monomer units are N-phenylacrylamide units.

In some embodiments of the invention the crosslinked polymer particles may be selected from the group consisting of crosslinked agarose particles, crosslinked cellulose particles, hydrophilic crosslinked vinyl polymer particles, and methacrylate based polymeric resin particles. In some embodiments of the invention the crosslinked polymer particle may be selected from the group consisting of Sepharose, Sephacel, Toyopearl, and Fractogel. In a specific embodiment of the invention, the crosslinked polymer particles are crosslinked agarose particles such as Sepharose particles.

In some embodiments the protein to be separated is selected from the group consisting of cytochrome C, lactoferrin, papain and lactoperoxidase. In a specific embodiment the protein is lactoferrin.

A further aspect of the invention is to provide crosslinked hydroxylic polymer particles functionalized with temperature-responsive copolymer, wherein the temperature-responsive copolymer includes a proportion of ionizable chemical groups. In some embodiments, temperature-responsive copolymer includes:

(ii) monomer units providing temperature-responsive properties to the copolymer; and (iii) monomer units providing ionizable chemical groups to the copolymer.

The monomer units providing temperature-responsive properties to the copolymer may be selected from the group consisting of N-isopropylacrylamide units, vinyl methyl ether units or N-vinylcaprolactam units. In a specific embodiment the monomer units providing temperature-responsive properties are N-isopropylacrylamide units.

The monomer units providing ionizable chemical groups may be selected from the group consisting of acrylic acid units, methacrylic acid units, ethacrylic acid units, sodium 2-acrylamido-2-methylpropanesulfonate units, sodium 3-acrylamido-3-methylbutanoate units, (3-acrylamidopropyl)trimethyl ammonium chloride units, N,N-dimethylaminopropylacrylamide units, N,N-dimethylaminoethyl methacrylate units, N,N-dimethylaminoethyl acrylate units, and 4-vinylbenzyltrimethylammonium chloride units. In a specific embodiment the monomer units providing ionizable chemical groups are acrylic acid units.

In a further embodiment of the invention, the temperature-responsive copolymer further includes at least one bi-functional monomer unit. The bi-functional monomer unit may be selected from the group consisting of ethylene glycol dimethacrylate units, 1,4-butanediol dimethacrylate units, 1,6-hexanediol dimethacrylate units, ethylene glycol diacrylate units, 1,4-butanediol diacrylate units, 1,6-hexanediol diacrylate units, and N,N-methylenebisacrylamide units. In a specific embodiment the bi-functional monomer unit are N,N-methylenebisacrylamide units.

In still another embodiment of the invention the temperature-responsive copolymer further includes at least one additional monomer unit. The additional monomer unit(s) may be selected from the group consisting of methyl acrylate units, ethyl acrylate units, propyl acrylate units, butyl acrylate units, methyl methacrylate units, ethyl methacrylate units, propyl methacrylate units, N-isopropylmethacrylamide units, butyl methacrylate units, N-tert-butylacrylamide units, N,N-dimethylacrylamide units, N,N-diethylacrylamide units, and N-phenylacrylamide units. In some specific embodiments, the additional monomer units are N-tert-butylacrylamide units. In other specific embodiments the additional monomer units are N-phenylacrylamide units.

In some embodiments the crosslinked hydroxylic polymer is selected from the group consisting of crosslinked agarose, crosslinked cellulose, hydrophilic crosslinked vinyl polymer, hydroxy-functional crosslinked vinyl polymer, hydroxy-functional crosslinked acrylic polymer and hydroxy-functional crosslinked methacrylic polymer. In preferred embodiments the crosslinked hydroxylic polymer is crosslinked agarose or hydrophilic crosslinked vinyl polymer. In one specific embodiment the crosslinked hydroxylic polymer is crosslinked agarose.

A further aspect of the present invention is to provide a method for preparing crosslinked hydroxylic polymer particles functionalized with temperature-responsive copolymer having a proportion of ionizable chemical groups, the method including:

(a) providing crosslinked hydroxylic polymer particles;

(b) chemically modifying the crosslinked hydroxylic polymer particles to provide crosslinked hydroxylic polymer particles having functional groups capable of initiating polymerization;

(c) contacting the crosslinked hydroxylic polymer particles having functional groups capable of initiating polymerization with a monomer solution including at least one monomer capable of providing temperature-responsive properties to the copolymer and at least one monomer capable of providing ionizable chemical groups to the copolymer, wherein said contacting initiates polymerization of the monomers;

(d) isolating crosslinked hydroxylic polymer particles functionalized with temperature-responsive copolymer having a proportion of ionizable chemical groups.

In some embodiments, the step of chemically modifying the crosslinked hydroxylic polymer particles to provide activated crosslinked hydroxylic polymer particles having functional groups capable of initiating polymerization includes the steps of (i) Functionalising the crosslinked hydroxylic polymer particles with an epoxide group;

(ii) Reacting the epoxide group with ammonia to provide crosslinked hydroxylic polymer particles functionalized with amine groups;

(iii) Reacting the amine groups with a polymerization initiator having at least one carboxylic acid group.

In a specific embodiment of the invention, the step of functionalizing the crosslinked hydroxylic polymer particles with an epoxide group includes reacting hydroxylic polymer particles with epichlorohydrin in the presence of sodium hydroxide and sodium borohydride. In a further embodiment, the step of reacting the amine groups with a polymerization initiator having a carboxylic acid group is conducted in the presence of a condensing agent. In a specific embodiment the condensing agent is 1-(ethoxycarbonyl)-2-ethoxy-1,2-dihydroquinoline.

In some embodiments the polymerization initiator having at least one carboxylic acid group is a peroxy initiator with a carboxylic acid group. In other embodiments the polymerization initiator having at least one carboxylic acid group is an azo initiator with a carboxylic acid group. In still other embodiments the polymerization initiator having at least one carboxylic acid group is a photoinitiator with a carboxylic acid group. In some embodiments of the invention, the polymerization initiator having at least one carboxylic acid group is 4,4'-azobis(4-cyanovaleric acid).

The monomer capable of providing temperature-responsive properties to the copolymer may be selected from the group consisting of N-isopropylacrylamide, vinyl methyl ether or N-vinylcaprolactam. In a specific embodiment the monomer capable of providing temperature-responsive properties is N-isopropylacrylamide.

The monomer capable of providing ionizable chemical groups may be selected from the group consisting of acrylic acid, methacrylic acid, ethacrylic acid, sodium 2-acrylamido-2-methylpropanesulfonate, sodium 3-acrylamido-3-methylbutanoate, (3-acrylamidopropyl)trimethyl ammonium chloride, N,N-dimethylaminopropylacrylamide, N,N-dimethylaminoethyl methacrylate, N,N-dimethylaminoethyl acrylate, and 4-vinylbenzyltrimethylammonium chloride. In a specific embodiment the monomer providing ionizable chemical groups is acrylic acid.

In a further embodiment of the invention, the monomer solution further includes at least one bi-functional monomer. The bi-functional monomer may be selected from the group consisting of ethylene glycol dimethacrylate, 1,4-butanediol dimethacrylate, 1,6-hexanediol dimethacrylate, ethylene glycol diacrylate, 1,4-butanediol diacrylate, 1,6-hexanediol diacrylate, and N,N-methylenebisacrylamide. In a specific embodiment the bi-functional monomer is N,N-methylenebisacrylamide.

In still another embodiment of the invention the monomer solution further includes at least one additional monomer. The additional monomer(s) may be selected from the group consisting of methyl acrylate, ethyl acrylate, propyl acrylate, butyl acrylate, methyl methacrylate, ethyl methacrylate, propyl methacrylate, N-isopropylmethacrylamide, butyl methacrylate, N-tert-butylacrylamide, N,N-dimethylacrylamide, N,N-diethylacrylamide, and N-phenylacrylamide. In some specific embodiments, the additional monomer is N-tert-butylacrylamide. In other specific embodiments the additional monomer is N-phenylacrylamide.

The step of contacting the crosslinked hydroxylic polymer particles having functional groups capable of initiating polymerization with a monomer solution including at least one monomer capable of providing temperature-responsive properties to the copolymer and at least one monomer capable of providing ionizable chemical groups to the copolymer typically occurs at a temperature at which the functional groups capable of initiating polymerization initiate polymerization. The specific temperature chosen will depend on the specific functional group capable of initiating polymerization, and will be readily evident to one having skill in the art. In some embodiments the temperature will be room temperature. In other embodiments the temperature may be chosen from the group consisting of 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., and 100° C. In a specific embodiment the temperature is 80° C. As will be appreciated by one having ordinary skill in the art, the density of the initiator groups on the particles may be varied.

In other embodiments the step of contacting the crosslinked hydroxylic polymer particles having functional groups capable of initiating polymerization with a monomer solution occurs under ultraviolet light. In still other embodiments the step of contacting the crosslinked hydroxylic polymer particles having functional groups capable of initiating polymerization with a monomer solution occurs under ionizing radiation. In still other embodiments the step of contacting the crosslinked hydroxylic polymer particles having functional groups capable of initiating polymerization with a monomer solution occurs under gamma radiation. In still other embodiments the step of contacting the crosslinked hydroxylic polymer particles having functional groups capable of initiating polymerization with a monomer solution occurs under X-ray radiation.

It will be appreciated by the skilled addressee that the invention can be modified for application to the separation of positively and negatively charged proteins. For example, the use of a monomer capable of providing ionizable chemical groups to the copolymer wherein those ionizable groups carry a negative charge when ionized will be applicable in the separation of proteins having a positive charge. Conversely, the use of a monomer capable of providing ionizable chemical groups to the copolymer wherein those ionizable groups carry a positive charge when ionized will be applicable in the separation of proteins having a negative charge.

As will be appreciated by the skilled addressee, the retention of the proteins by the functionalized crosslinked particles means that the proteins associate with the particles to the extent that they are removed from the solution to be purified. It will also be appreciated by the skilled addressee that, in addition to electrostatic (i.e. positive/negative) interactions between the particles and the proteins, other interactions between the particles and the protein can occur. For instance, metal-ligand interactions, hydrophobic interactions, hydrogen bonding interactions, stereocomplexation interactions or charge transfer interactions may also contribute to interaction between the protein and the particles of the invention which causes retention of the proteins on the particles of the invention.

The temperature at which the protein solution is contacted with the crosslinked polymer particles functionalized with temperature-responsive copolymer having a proportion of ionizable chemical groups can be varied as appropriate for the particular temperature-responsive copolymer and the particular protein being separated. The temperature will be such that a proportion of the protein will be retained by the functionalized crosslinked polymer particles, Typically the temperature will be between 30° C. and 80° C. in some embodiments the temperature will be between 30° C. and 60° C., and in further embodiments the temperature will be between 45° C. and 55° C. In some embodiments the temperature at which the protein solution is contacted with the crosslinked polymer particles is chosen from the group consisting of 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C. and 80° C. In other embodiments, the temperature is chosen from the group consisting of 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., and 60° C. In still other embodiments, the temperature is chosen from the group consisting of 45° C., 46° C., 47° C., 48° C., 49° C., 50° C., 51° C., 52° C., 53° C., 54° C. and 55° C. In some specific embodiments, the temperature at which the protein is contacted with the functionalized crosslinked polymer particles is 50° C. In other specific embodiments the temperature at which the protein is contacted with the functionalized crosslinked polymer particles is 40° C. In still other specific embodiments the temperature at which the protein is contacted with the functionalized crosslinked polymer particles is 60° C.

Subsequent exposure of the particles to the rinse solution may take place at the same temperature as the original contacting with the protein solution, at higher temperature or at lower temperature. The temperature of the rinse solution is such that a proportion of the protein will be retained by the functionalized polymer particles while the particles are exposed to the rinse solution. Typically the temperature of the rinse solution will be between 30° C. and 80° C. In some embodiments the temperature will be between 30° C. and 60° C., and in further embodiments the temperature will be between 45° C. and 55° C. In some embodiments temperature of the rinse solution is chosen from the group consisting of 30° C., 31° C., 32° C., 33° C., 34° C., 35° C., 36° C., 37° C., 38° C., 39° C., 40° C., 41° C., 42° C., 43°

C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C. and 80° C. In other embodiments, the temperature of the rinse solution is chosen from the group consisting of 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C. and 60° C. In still other embodiments, the temperature of the rinse solution is chosen from the group consisting of 45° C., 46° C., 47° C., 48° C., 49° C., 50° C., 51° C., 52° C., 53° C., 54° C. and 55° C. In some specific embodiments, the temperature of the rinse solution is 50° C. In other specific embodiments the temperature of the rinse solution is 40° C. In still other specific embodiments the temperature of the rinse solution is 60° C.

Subsequent exposure of the particles to the release solution typically takes place at a temperature lower than the original contacting with the protein solution. The temperature of the release solution is such that a proportion of the protein is released from the functionalized polymer particles into the release solution. Typically the temperature of the release solution will be between 0° C. and 80° C. In some embodiments the temperature will be between 0° C. and 30° C. In other embodiments the temperature will be between 0° C. and 20° C. In still other embodiments the temperature will be between 0° C. and 10° C. In some embodiments the temperature of the release solution is chosen from the group consisting of 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C. and 30° C. In other embodiments the temperature of the release solution is chosen from the group consisting of 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C. and 20° C. In still other embodiments the temperature of the release solution is chosen from the group consisting of 0° C., 1° C., 2° C., 3° C., 4° C., 5° C., 6° C., 7° C., 8° C., 9° C., 10° C. In some specific embodiments the temperature of the release solution is 20° C. In other specific embodiments the temperature of the release solution is between 0° C. and 4° C.

In some cases the release solution contains no ionic solute. In some cases the release solution contains an ionic solute. The ionic solute may be any ionic solute known in the art which is soluble in the release solution. In some preferred embodiments the ionic solute is an alkali metal halide or alkali earth metal halide. In a more preferred embodiment, the ionic solute is a lithium, sodium or potassium halide. In an even more preferred embodiment the ionic solute is lithium chloride, potassium chloride, sodium chloride, lithium bromide, potassium bromide, sodium bromide, lithium iodide, potassium iodide or sodium iodide. In a most preferred embodiment the ionic solute is sodium chloride.

In some instances it is desirable to vary the concentration of the ionic solute in the release solution when contacting with the crosslinked polymer particles functionalized with temperature-responsive copolymer having a proportion of ionizable chemical groups. The concentration of the ionic solute in the release solution may be any concentration between 0 M and 2 M. In some embodiments the concentration of the ionic solute in the release solution may be any concentration between 0 M and 1 M. In some particular embodiments the concentration of the ionic solute may be varied from 0 M to 0.01 M to 0.1 M to 1.0 M. The variation may be continuous, incremental or stepped. In some specific embodiments the concentration is stepped from 0 M to 0.1 M to 1.0 M NaCl.

The proportion of monomer units providing ionizable chemical groups to the copolymer, monomer units providing temperature-responsive properties to the copolymer, bi-functional monomer units and additional monomer units may be varied depending on the specific operating conditions required and/or the requirements of the protein to separated. In some embodiments, the bi-functional monomer unit may be omitted. In other embodiments, the additional monomer unit may be omitted. In still further embodiments, both the bi-functional monomer unit and the additional monomer unit are omitted. In some embodiments, the ratio of the temperature-responsive monomer units to the additional monomer units to the monomer units providing ionisable groups is from 80:10:10 to 98:1:1. In other embodiments, the ratio of the temperature-responsive monomer units to the additional monomer units to the monomer units providing ionisable groups is from 84:8:8 to 96:2:2. In some specific embodiments, the temperature responsive monomer units are N-isopropylacrylamide units, the additional monomer units are tert-butylacrylamide units and the monomer units providing ionisable groups are acrylic acid units and the ratio of the N-isopropylacrylamide units tert-butylacrylamide units:acrylic acid units is from 80:10:10 to 98:1:1. In other specific embodiments, the temperature responsive monomer units are N-isopropylacrylamide units, the additional monomer units are N-phenylacrylamide units and the monomer units providing ionisable groups are acrylic acid units and the ratio of the N-isopropylacrylamide units:N-phenylacrylamide units:acrylic acid units is from 80:10:10 to 98:1:1. In some other specific embodiments, the temperature responsive monomer units are N-isopropylacrylamide units, the additional monomer units are tert-butylacrylamide units and the monomer units providing ionisable groups are acrylic acid units and the ratio of the N-isopropylacrylamide units:tert-butylacrylamide units:acrylic acid units is from 84:8:8 to 96:2:2. In still other specific embodiments, the temperature responsive monomer units are N-isopropylacrylamide units, the additional monomer units are N-phenylacrylamide units and the monomer units providing ionisable groups are acrylic acid units and the ratio of the N-isopropylacrylamide units:N-phenylacrylamide units: acrylic acid units is from 84:8:8 to 96:2:2.

The methods of the invention may be applied in the separation of any protein of interest in the food, pharmaceutical, chemical and water industries, or any other industry. Proteins which may be suitable for separation by the invention include antibodies; non-antibody proteins; immunoglobulins; immunoglobulin-like proteins; non-human growth factors; enzymes; hormones; cytokines; Fc-derivatised proteins; and recombinant antigens. Other candidates include granulocyte-colony stimulating factor (GCSF), stem cell factor, leptin, hematopoietic factors, non-human growth factors, antiobesity factors, trophic factors, anti-inflammatory factors, receptors or soluble receptors, enzymes, variants, derivatives, or analogs of any of these proteins. Other examples include insulin, gastrin, prolactin, adrenocorticotropic hormone (ACTH), thyroid stimulating hormone (TSH), luteinizing hormone (LH), follicle stimulating hormone (FSH), human chorionic gonadotropin (HCG), motilin interferons (alpha, beta, gamma, omega), interleukins (IL-1 to IL-12), tumor necrosis factor (TNF), tumor necrosis factor-binding protein (TNF-bp), brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), insulin-like growth factors (IGFs), macrophage colony stimulating factor (M-CSF), granulocyte macrophage colony stimulating factor (GM-CSF), megakaryocyte derived growth factor (MGDF), keratinocyte growth factor (KGF), erythropoietin, thrombopoietin, platelet-derived growth factor (PGDF), colony simulating growth factors (CSF's), bone morphogenetic protein (BMP), superoxide dismutase (SOD), urokinase, streptokinase, or kallikrein, receptors or soluble receptors, enzymes, variants, derivatives, or analogs of any of these proteins. Other examples include albumen, serum albumin, insulin, ribonuclease A, myoglobin, chymotrypsin, trypsin, chymotrypsinogen, hemoglobin, hexokinase, immunoglobulin G, RNA polymerase, DNA polymerase, apolipoprotein B, glutamate dehydrogenase, lipoproteins, glycoproteins, phosphoproteins, hemoproteins, flavoproteins and metalloproteins. In some preferred embodiments the proteins suitable for separation with the invention include lactoferrin, lactoperoxidase and papain. In some specific embodiments of the invention the protein is lactoferrin.

One feature of the invention is that the ionizable groups are provided by the incorporation of monomer units having ionizable chemical groups as part of the temperature responsive copolymer (i.e., not from or by modification of the hydroxylic polymer substrate particle). This is distinct from other approaches wherein there may be separate modification of the substrate particles to provide ionizable groups which are independent of the temperature responsive copolymer. For instance, in the case of agarose particles functionalized with poly(N-isopropylacrylamide-co-tert-butylacrylamide-co-acrylic acid), the ionizable groups are provided by the acrylic acid monomer units in the polymer, rather than by direct modification of the agarose substrate particle.

The polymer particle functionalized with temperature-responsive copolymer having a proportion of ionizable chemical groups may be stable to alkaline cleaning conditions employed in the food, pharmaceutical, chemical, water and other industries. Additionally, the nature of the polymer particle may be varied to accommodate process variables, such as extremes of pH or high concentrations of solute.

EXAMPLES

Materials

Crosslinked agaraose particles (Sepharose® 6 fast flow) were obtained from Pharmacia Biotech (Sweden), lactoferrin sample was provided by Food Science Australia (Werribee). N-isopropylacrylamide (97%), tert-butylacrylamide (97%), acrylic acid (≥98%), 1-(ethoxycarbonyl)-2-ethoxy-1,2-dihydro-quinoline (≥99%), 4,4'-azo bis(4-cyanovaleric acid) (≥98%), N,N-dimethylformamide (≥99.8%) and N,N'-methylenebisacrylamide (≥98%) were obtained from Sigma Aldrich (USA).

Preparation of Crosslinked Agarose Particles of the Invention

A polymerisation initiator, 4,4'-azobis(4-cyanovaleric add) (ACV), was covalently immobilized onto the amino functionalised Sepharose 6 FF using N,N-dimethylformamide (DMF) as the solvent and 1-(ethoxycarbonyl)-2-ethoxy-1,2-dihydroquinoline (EEDQ) as the condensing agent (adapted from Yakushiji et al., *Anal. Chem.*, 1999, 71, 1125-1130). Across-linked polymer matrix was developed on the ACV immobilized Sepharose by radical polymerization using N-isopropylacrylamide (NIPAAm), acrylic acid (AAc) and tert-butylacrylamide (tBAAm) as monomers and N,N'-methylenebisacrylamide (MBBA) as the cross linking agent. The particles were denoted as ItBA.

The details of the synthesis steps are as described below
1. Amino Functionalisation of Sepharose 6 FF
1.1 Activation of Sepharose 6 FF with Epichlorohydrin Sepharose 6 FF (100 g) was collected on sintered glass funnel and washed with distilled water (5× volume of wet gel). The washed gel was suction dried and transferred into a 500 mL Schott bottle. A 2 M NaOH solution (100 mL) containing $NaBH_4$ (0.187 g) was added and the suspension was mixed at 28° C. for 2 h on a rocking platform at a speed of 175 rpm. Epichlorohydrin (60 mL) was added to the gel slurry, which was then mixed at 28° C. for another 21 h on a rocking platform at a speed of 175 rpm. The epoxy activated gel was then collected by vacuum filtration and washed with distilled water.

1.2 Coupling Epoxy-Activated Sepharose with Aqueous Ammonia

Epoxy-activated Sepharose (95 g) was collected on sintered glass funnel and washed with distilled water (5× volume of wet gel). The washed gel was suction dried and transferred into a 500 mL Schott bottle. A 2 M aqueous ammonia solution (95 mL) was added. The slurry was mixed at 28° C. for 21 h on a rocking platform. The aminated Sepharose gel was collected by vacuum filtration and washed with copious amounts of distilled water until the pH of the filtrate was <8. The gel was then stored in 20% v/v aqueous ethanol at 4° C. until further use.

2. Immobilisation of the Polymerization Initiator

ACV (20.25 mmol, 5.67 g) and EEDQ (40.5 mmol, 10.01 g) were dissolved in DMF (270 mL) in a 500 mL 3-necked round bottom flask. Amino functionalised Sepharose (90 g) was washed with 50%, 75% and 100% ethanol (100 mL each) respectively. The gel was added to the solution containing ACV and EEDQ. The slurry mixture was declassed by bubbling nitrogen for 45 min followed by application of vacuum (3 min). The coupling reaction was then carried out under argon atmosphere at 25° C. for 6 h with constant stirring using an IKA® overhead stirrer (RW20, IKA Labortechnik). The ACV immobilized gel was collected on a sintered glass funnel and washed with DMF and ethanol. The gel was then stored in 20% v/v aqueous ethanol at 4° C. until further use.

3. Developing the Polymer Matrix on the ACV Immobilized Sepharose

NIPAAm (112.5 mmol, 12.73 g), tBAAm (6.25 mmol, 0.79 g), AAc (6.25 mmol, 0.43 mL) and MBBA (1.25 mmol, 0.19 g) were dissolved in ethanol (125 mL) in a 250 mL 3-necked round bottom flask. ACV immobilized Sepharose FF (25 g, washed with 20%, 50%, 75% and 100% ethanol) was added to the solution mixture. The mixture was degassed by bubbling nitrogen for 30 min followed by application of vacuum (3 min). The polymerisation reaction was carried out in argon atmosphere at 80° C. for 16 h with constant stirring using an IKA® overhead stirrer. The gel was collected on a sintered glass funnel and washed with 100%, 75% 50%, 20% ethanol respectively and finally with cold water. The gel was then stored in 20% v/v aqueous ethanol at 4° C. until further use.

3.1 Characterization of the ItBA Using $^1H$ NMR

The ratio of NIPAAm and tBAAm in the copolymer was estimated from $^1H$-NMR spectral data obtained using a Bruker 400 MHz NMR spectrometer with $CDCl_3$ as the solvent.

The $^1$H NMR spectra was obtained using free copolymer from the supernatant obtained during the particle functionalisation process. The $^1$H NMR spectra of the free copolymer in CDCl$_3$ confirmed that the ratio of NIPAAm to tBAAm in the free copolymer was 23:2. Assuming that the composition of the free copolymer in solution examined was similar to that of the copolymer immobilised onto the resin, the ratio of the monomers (NIPAAm:tBAAm:AA) on the ItBA resin can be estimated to be 86:8:6, which is similar to the monomer ratio (90:5:5) employed in the polymerisation process.

3.2 Characterization of the ItBA Using Elemental Analysis

The total combined NIPAAm and tBAAm content of ItBA was determined using elemental nitrogen analysis (Carlo Erba Elemental Analyser EA 1108, Thermo Fisher Scientific, Milan, Italy). Using this analysis, the combined content of NIPAAm and tBAAm present in the ItBA was determined to be 2060±62 µmol/g of freeze dried gel.

3.3 Characterization of the LCST of ItBA Using UV Visible Spectroscopy

The lower critical solution temperature of the copolymer was determined by measuring the optical transmittance of a 0.5% (w/w) aqueous copolymer solution at 500 nm between 24° C. and 38° C. using a UV/visual spectrometer (SpectraMax Plus, Molecular Devices, Sunnyvale, USA) with a temperature controlled cuvette chamber. The copolymer characterized was derived from the supernatant obtained during the particle functionalisation process.

The LCST of ItBA was estimated by investigating the optical transmittance of copolymer from the supernatant obtained during the particle functionalisation process. The LCST was determined by observing the temperature at which the optical transmittance of the copolymer solution is 50% of the maximal value, when the polymer solution is subject to a temperature gradient. The LCST of the free (bulk) ItBA copolymer (poly(NIPAAm-co-AAc-co-tBAAm)) produced in the reaction solution was found to be at 30° C. Assuming that the composition of the copolymer within the ItBA is similar to that for the free species in the reaction solution, the LSCT of the copolymer on the ItBA resin should be approximately 30° C.

4. Method for Production of CM Sepharose

Sepharose 6 FF (15 g) was collected on sintered glass funnel and washed with distilled water (5× volume of wet gel). The washed gel was suction dried and transferred into a 50 mL falcon tube. 11M NaOH (15 mL) was added to the tube and mixed for 45 min using a rotating wheel (Ratek, Australia) at 28° C. Then 1.4M chloroacetic acid (15 mL) was added to the tube and mixed for another 3 h. Finally the resin was collected by vacuum filtration and washed with copious amounts of distilled water, unto the pH of the filtrate was <8. The gel was then stored in 20% v/v aqueous ethanol at 4° C. until further use. The carboxymethyl modified Sepharose 6 FF was designated CM.

5. Characterisation of the ItBA and CM Using Base Titration

The acid group concentration on the developed resins was determined by titration of the resin with 0.02 M NaOH and monitoring the pH using a Metrohm autotitrator (Metrohm Titrando 808, Switzerland). The concentration of add groups attached to the resins was reported in µmol/g freeze dried resin.

The concentration of acidic groups on the ItBA and CM resins were 154±7 µmol/g freeze dried gel and 171±4 µmol/g freeze dried gel, respectively.

6. Applying Temperature-Responsive Agarose Particles in Protein Separation 6.1 Equilibrium Adsorption Isotherms 6.1a Adsorption Isotherm for Lactoferrin In order to demonstrate the effectiveness of the developed thermally responsive cation exchange resin (ItBA) to retain differentially at low and high temperature, equilibrium adsorption isotherms for lactoferrin with ItBA were determined at 20° C. and 50° C. (FIG. 1). As a control experiment, equilibrium adsorption isotherms were also obtained for carboxymethyl Sepharose (CM) with a similar ion exchange capacity to that of ItBA.

For CM there was no significant difference between the adsorption isotherms at 20° C. and 50° C. The $B_{max}$ values for CM at 20° C. and 50° C. were 76±2 mg/mL and 78±2 mg/mL respectively. For ItBA there was a significant difference between adsorption isotherms at 20° C. and 50° C., and the $B_{max}$ value at 50° C. (24±2 mg/mL) was approximately 3 times higher than the $B_{max}$ value at 20° C. (68±2 mg/mL) (FIG. 1). The observed increased in $B_{max}$ at 50° C. indicates the potential of ItBA to use as a thermally responsive ion exchange resin.

6.1b Adsorption Isotherm for Lactoperoxidase

Lactoperoxidase was also used to determine adsorption isotherms with ItBA prepared via the method described above. Lactoperoxidase solutions (1 mg/mL, 5 mg/mL, 10 mg/mL, 20 mg/mL, and 40 mg/mL) were prepared in 10 mM phosphate buffer (pH 6.5). 500 µl aliquots were mixed with 0.05 g samples for 35 min at 20° C. or 50° C. The protein solution and resin samples for incubation at 50° C. were pre-equilibrated to 50° C. prior to mixing.

Figure 2:
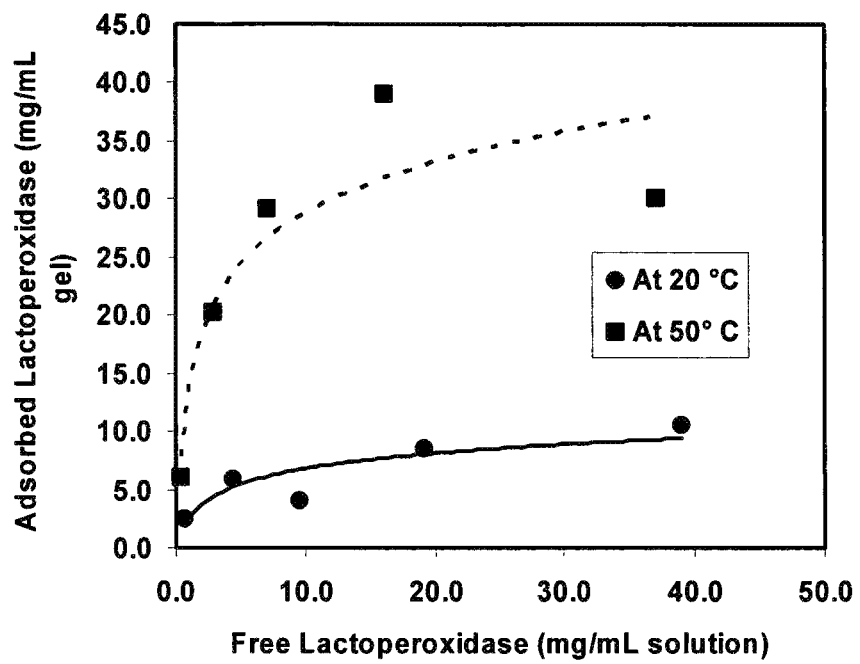
FIG. 2 shows lactoperoxidase adsorption isotherms for ItBA at 20° C. and 50° C.

The mixtures were then allowed to sediment for 10 minutes at 20° C. or 50° C. and the supernatant was removed. The supernatants were centrifuged at 15,000×g for 3 min. The lactoperoxidase concentration in the supernatant was determined by measuring the absorbance at 280 nm. The maximum retention capacity $B_{max}$ was then calculated from the adsorption isotherms. The adsorption isotherms in FIG. 2 are an average of three experiments, a different batch of resin was used each time.

It can be seen that there was a significant difference between adsorption isotherms of lactoperoxidase with ItBA at 20° C. and 50° C. The $B_{max}$ values were 11±5.8 mg/mL and 37±5.7 mg/mL, respectively (FIG. 2).

6.1c Adsorption Isotherm for Papain

Figure 3:
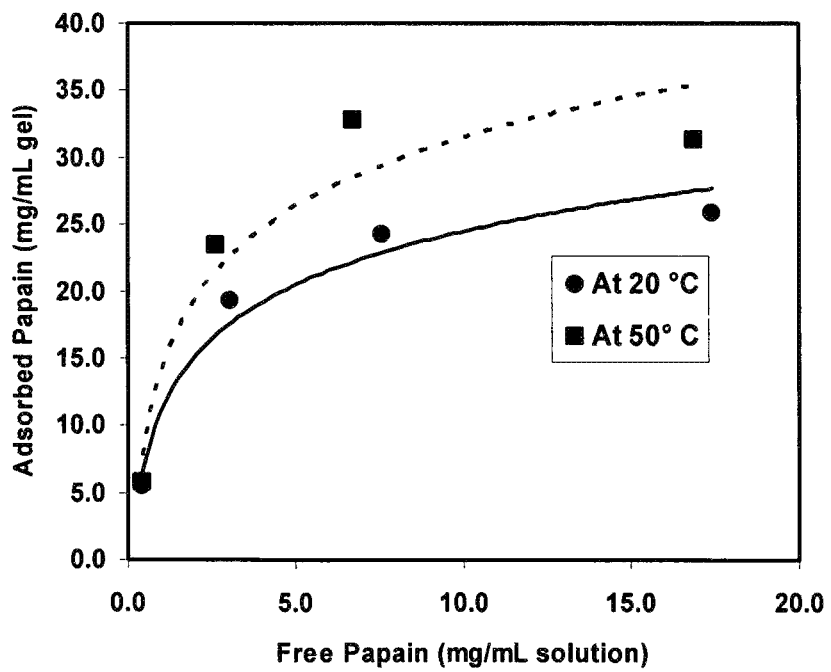
FIG. 3 shows papain adsorption isotherms for ItBA at 20° C. and 50° C.

Papain was also used to determine adsorption isotherms with ItBA prepared via the method described above. Adsorption isotherms for papain were prepared similarly to lactoperoxidase, with the exception that the samples incubated at 50° C. were not pre-equilibrated at 50° C. prior to mixing. The maximum retention capacity $B_{max}$ was then calculated from the adsorption isotherms. The adsorption isotherms in FIG. 3 are an average of three experiments, with a different batch of resin being used for each experiment.

There was a difference in ItBA adsorption isotherms of papain at 20° C. and 50° C. The $B_{max}$ values for 20° C. and 50° C. were 28.9±4.4 and 36.9±4, respectively (FIG. 3).

Figure 4:
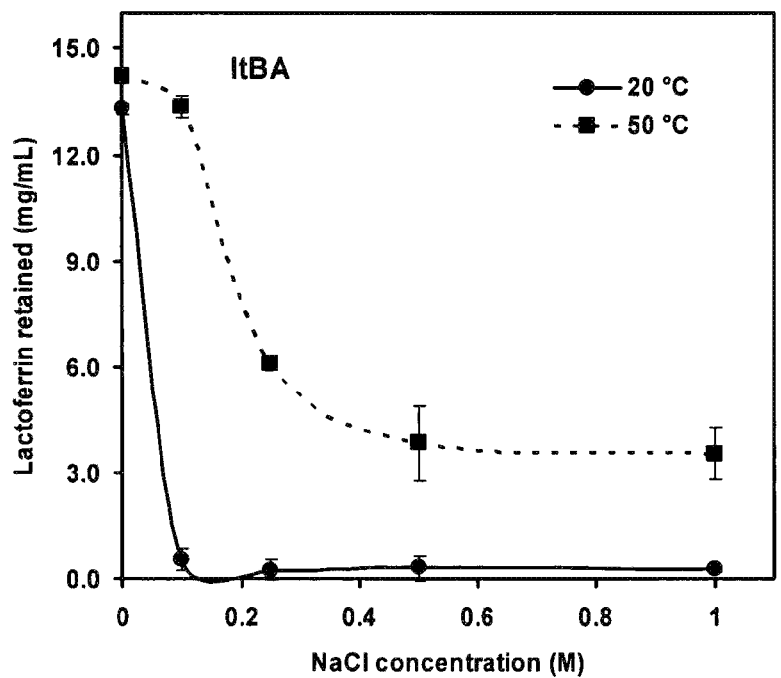
FIG. 4 shows the effect of salt concentration on retention of lactoferrin on ItBA and CM at 20° C. and 50° C., respectively.
Figure 4:
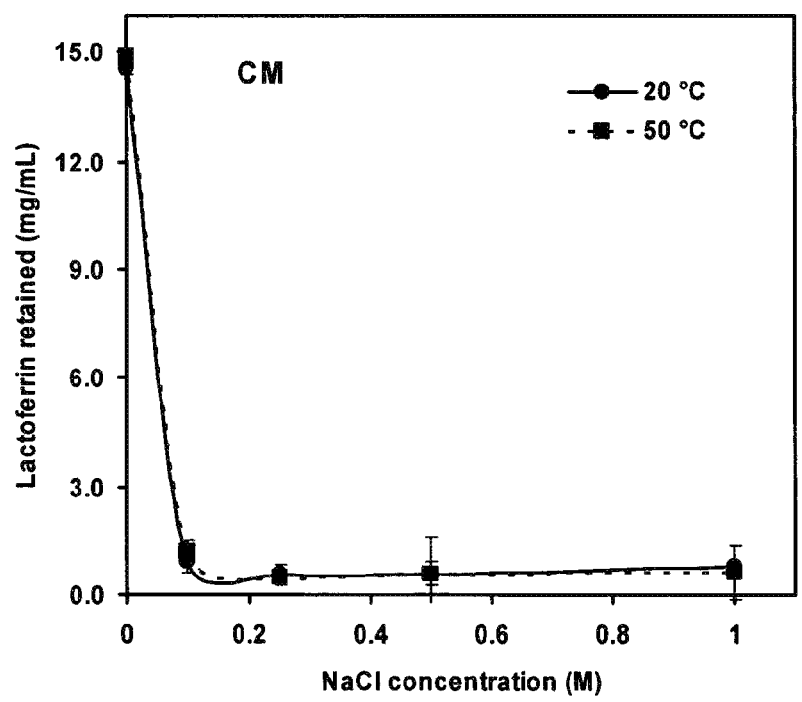

6.2 Retention at Various Salt Concentrations 6.2a Comparative Studies Between ItBA and CM at Various Salt Concentrations The presence of salt disrupts the electrostatic interaction between the protein and the ion exchange groups on the resin, thereby reducing the rate and capacity of the ion-exchanger for protein adsorption (Yamamoto, et al. 1988). The presence of salt is known not to reduce hydrophobic interactions. To get a better understanding of the interaction mechanism between lactoferrin and the resin, retention studies were conducted at various salt concentrations. The results are as shown in FIG. 4.

In the case of CM there was no significant difference between the retention profiles at low and high temperature. At both temperatures, NaCl solution of 0.1 M or higher concentration almost completely inhibited the retention of lactoferrin to CM. This suggests that there is an ionic interaction between the CM and lactoferrin at both 20° C. and 50° C.

ItBA showed significantly different retention behaviour at 20° C. and 50° C. when the salt concentration was changed. At 20° C. almost complete inhibition of lactoferrin retention was observed at 0.1M, which suggests that at lower temperature ionic interaction is the principal force for protein retention onto the resin. However, at 50° C., 0.25M or higher concentrations of NaCl were required to obtain a significant drop in the amount of protein retained by the resin, which suggests that at high temperatures there is a stronger ionic interaction between the resin and the protein. Furthermore, at 50° C. and 1M NaCl there was still retention of protein. This indicates that even though ionic interaction is the principal force, there are other forces which are contributing to retention of the proteins, possibly hydrophobic interactions between hydrophobic regions of the protein and the collapsed hydrophobic polymer matrix.

6.2b Effect of Low Salt Concentrations on Lactoferrin Retention by ItBA

The effect of small differences in sodium concentration on the static retention of lactoferrin to ItBA were investigated by mixing lactoferrin solutions containing 20 mM or approximately 13 mM sodium with the resin (0.05 g) for 35 min at 20° C. and 50° C. The mixtures were then allowed to sediment for 10 minutes at 20° C. or 50° C. and the supernatant was removed. The supernatants were centrifuged at 15,000×g for 3 min. The lactoferrin concentration in the supernatants were determined by measuring the absorbance at 280 nm. The maximum retention capacity $B_{max}$ was then calculated from the adsorption isotherms.

Figure 5:
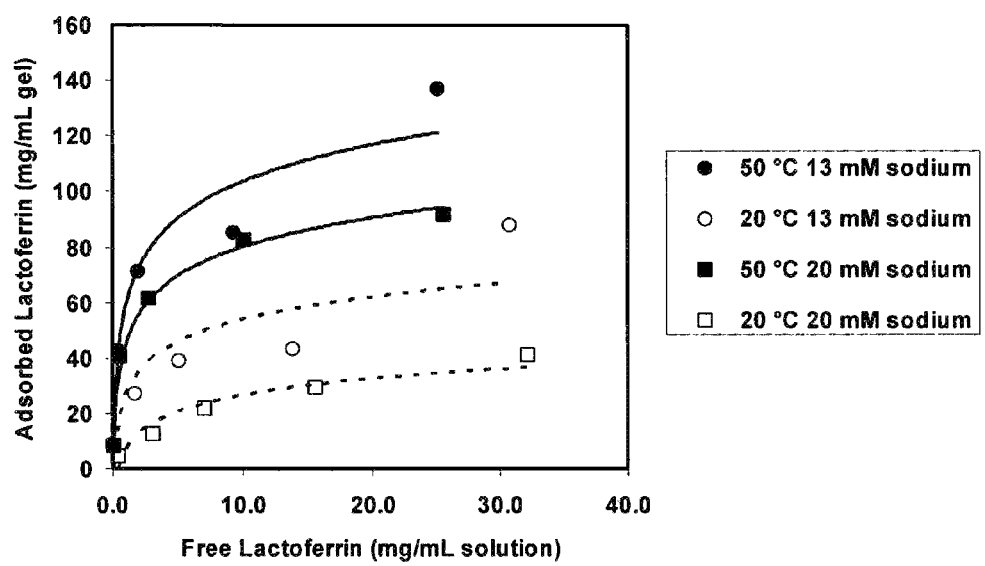
FIG. 5 shows the effect of sodium concentration on ItBA retention of lactoferrin at 20° C. and 50° C. Results are shown for 13 mM and 20 mM sodium.

The retention of lactoferrin by ItBA was greater in sodium concentration of approximately 13 mM at 20° C. and 50° C. than that at sodium concentration of 20 mM (FIG. 5). Thus, lower sodium concentrations increased the maximal retention capacity of the resin at both 20° C. and 50° C.

6.3 Dynamic Retention and Elution of Lactoferrin

One of the most promising applications of ItBA involves contacting a solution of the target protein at 50° C., resulting in retention of the target protein and then release of a proportion of the retained material simply by dropping the temperature to 20° C.

Resins were packed into PEEK columns (100×4.6 mm i.d.) and the dynamic retention and release characteristics of lactoferrin were studied at 20° C. and 50° C. The system used for dynamic studies was a Waters 2525 HPLC pump, Waters 2767 sample manager and Waters diode-array detector. The temperature of the column was maintained by immersing a spiral metal tubing (heat exchange zone) and the column into a water bath set at the required temperature. The aqueous mobile phase employed was pH 6.5 phosphate buffer or 1M NaCl.

Figure 6:
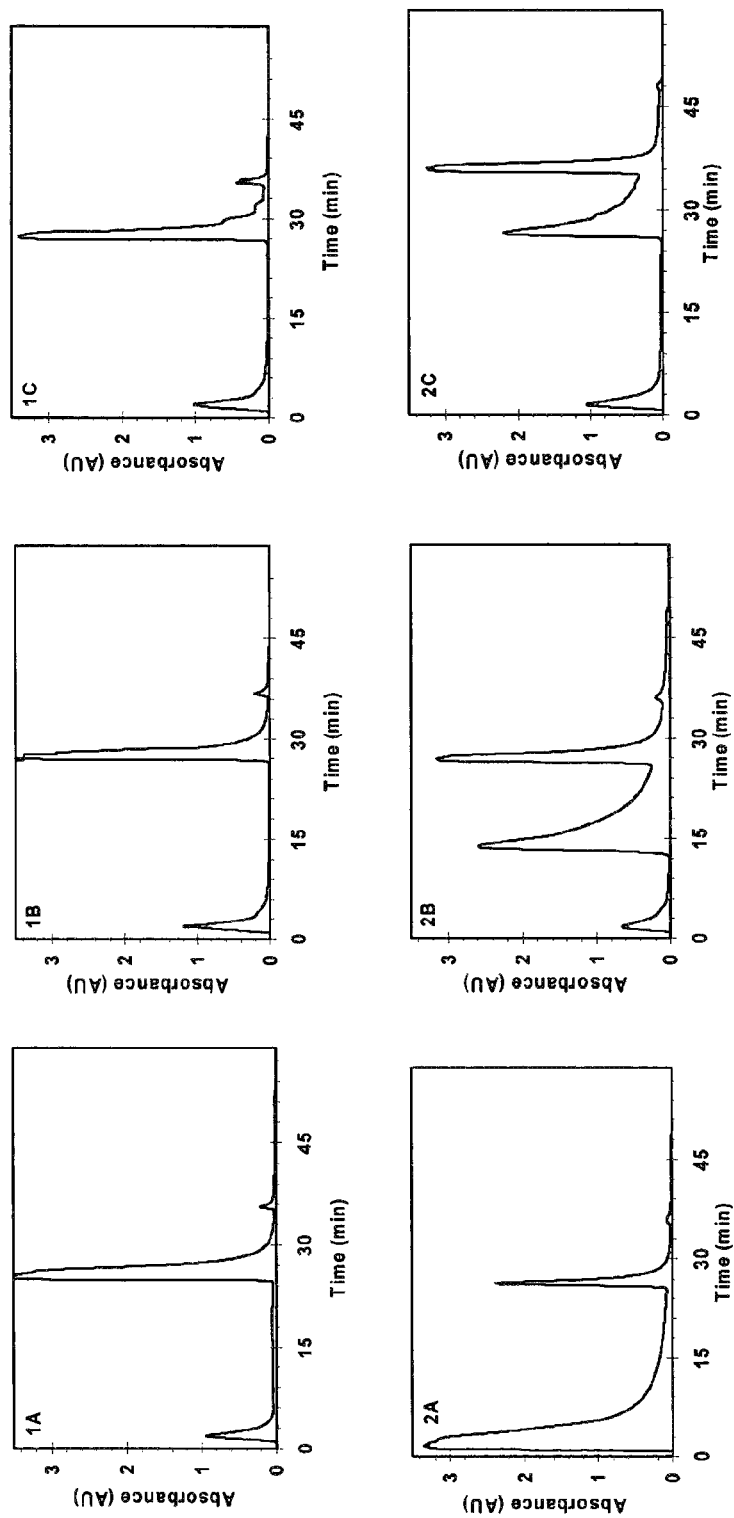
FIG. 6 includes chromatograms produced when lactoferrin is loaded dynamically onto CM (1) and ItBA (2) A: at 20° C. for 12 minutes (0-12 min), followed by elution at 20° C. for 10 minutes (12-22 min), followed by 0.1M NaCl for 10 minutes (23-33 min), and 1M NaCl for 10 minutes (35-45 min), B: at 50° C. for 12 minutes (0-12 min), followed by elution at 20° C. for 10 minutes (12-22 min), followed by 0.1M NaCl for 10 minutes (23-33 min), and 1M NaCl for 10 minutes (35-45 min) and C: at 50° C. for 12 minutes (0-12 min) followed by elution at 50° C. for 10 minutes (12-22), followed by 0.1M NaCl for 10 minutes (23-33 min), and 1M NaCl for 10 minutes (35-45 min).

The chromatograms in FIG. 6 and data in Table 1 illustrate ti e potential of ItBA resins to retain lactoferrin, and then release a large proportion of the retained lactoferrin by decreasing the temperature. During the dynamic retention and release study of the developed resins, it was found that for CM there was no significant difference between the chromatograms at three different testing conditions (A—contacting at 20° C. and elution at 20° C.; B—contacting at 50° C. and elution at 20° C. and C—contacting at 50° C. and elution at 50° C.). The effect of temperature on the retention and release of protein onto CM was not significant. However, for ItBA the chromatograms at the three different conditions were distinctively different. The retention capacity of the resin significantly improved when the contacting temperature was increased from 20° C. to 50° C. When protein was contacted at 50° C. almost 50% of the retained protein could be eluted by dropping the column temperature to 20° C. When release was undertaken at 50° C., higher concentrations of NaCl were required to release most of the retained proteins, suggesting that at 50° C. there is a stronger interaction between the resin and analyte.

TABLE 1

Percentage of protein (lactoferrin) collected in various fractions after dynamic retention and release using CM or ItBA

| | % of the injected lactoferrin (28 mg) in various collection fractions | | | | | |
|---|---|---|---|---|---|---|
| | Flow through | Temperature change | 0.1M NaCl | 1M NaCl | Re-equilibration | Total |
| | | | Time | | | |
| | 0-12 min | 12-22 min | 23-33 min | 35-45 min | 47-59 min | recovery |
| CM | | | | | | |
| Contacting at 20° C. and elution at 20° C. | 6 | 1 | 89 | 3 | 0 | 99 |
| Contacting at 50° C. and elution at 20° C. | 9 | 1 | 88 | 2 | 0 | 100 |
| Contacting at 50° C. and elution at 50° C. | 7 | 0 | 86 | 7 | 0 | 100 |
| ItBA | | | | | | |
| Contacting at 20° C. and elution at 20° C. | 71 | 7 | 16 | 5 | 0 | 99 |
| Contacting at 50° C. and elution at 20° C. | 4 | 47 | 39 | 4 | 1 | 95 |
| Contacting at 50° C. and elution at 50° C. | 6 | 1 | 40 | 43 | 1 | 92 |

7. Alternative Formulations of Temperature-Responsive Agarose Particles

N-Vinyl caprolactam is also a monomer which has been employed to manufacture temperature responsive polymers with LCST values similar to N-isopropylacrylamide polymers. It is a cheaper alternative to N-isopropylacrylamide that may be employed to manufacture temperature responsive ion exchange resins, N-phenylacrylamide is a more hydrophobic monomer when compared to the co-monomers tert-butylacrylamide and butyl methacrylate. N-phenylacrylamide may also be employed as a co-monomer to manufacture temperature responsive on exchange resins with improved temperature sensitivity and retention capacity.

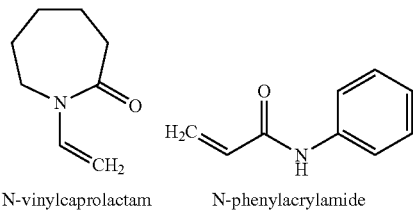

N-vinylcaprolactam    N-phenylacrylamide

Figure 7:
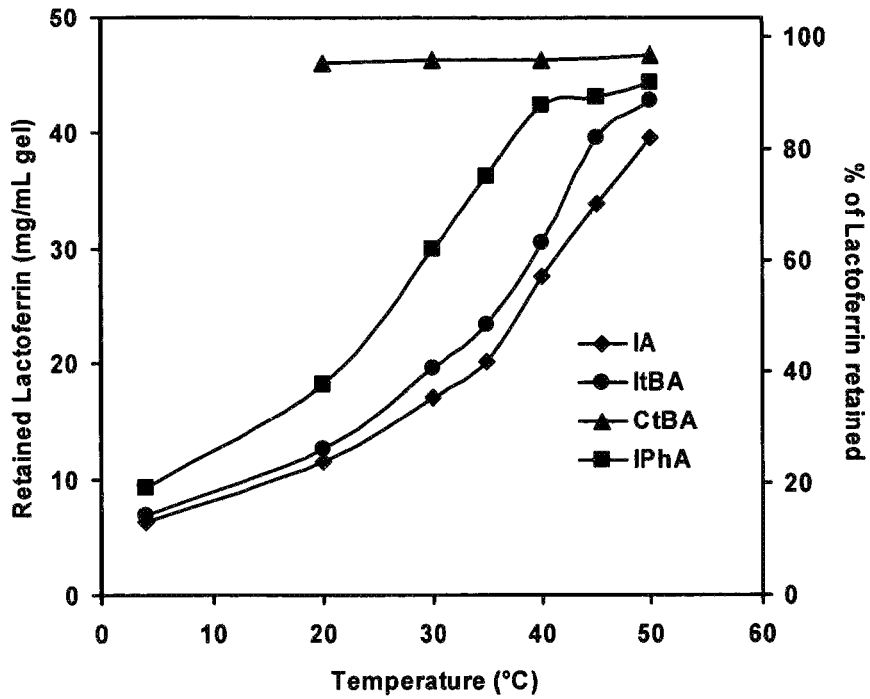
FIG. 7 shows the amount of lactoferrin retained (mg/mL resins and % of total) by four different resin formulations at temperatures between 4 and 50° C. The resins are poly(N-isopropylacrylamide-co-acrylic acid) (IA), ItBA, poly(N-vinylcaprolactam-co-N-tert-butylacrylamide-co-acrylic acid) (CtBA) and poly(N-isopropylacrylamide-co-N-tert-butylacrylamide-co-acrylic acid) (IPhA).

The possibility of manufacturing temperature responsive ion-exchange resins in an economical way was explored by using N-vinylcaprolactam as the temperature responsive monomer. The use of N-phenylacrylamide as a co-monomer to manufacture temperature responsive ion-exchange resins with improved temperature sensitivity and retention capacity was also explored. ItBA was manufactured as described above. However, during the manufacturing process NIPAAm was replaced with N-vinylcaprolactam to make Sepharose based poly(N-vinylcaprolactam-co-N-tert-butylacrylamide-co-acrylic acid) (CtBA). In a second manufacturing process tBAAm was removed from the formulation and replaced by the more hydrophilic monomer NIPAAm to make Sepharose based poly(N-isopropylacrylamide-co-acrylic acid) (IA). In a third manufacturing process, tBAAm was replaced by the more hydrophobic monomer N-phenylacrylamide to make Sepharose-based poly(N-isopropylacrylamide-co-N-phenylacrylamide-co-acrylic acid) (IPhA). The effect of changing the polymer composition on the lactoferrin retention profile was examined using a static retention methodology. Resin (0.1 g) was mixed with lactoferrin solution (1 mL of 5 mg/mL) for 1 h at temperatures between 4° C. and 50° C. The resin was allowed to settle and the amount of unretained protein was determined by measuring the absorbance of the supernatant at 280 nm, which in turn gave the amount of protein retained by the resins. Results are shown in FIG. 7.

CtBA retained more than 95% of the available lactoferrin at all tested temperatures. At 4° C., all three other resins (IA, ItBA and IPhA) retained less than 20% of the available lactoferrin. At 50° C. the same three resins retained 80% or more of the available lactoferrin. Amongst these temperature responsive resins, IA retained the least amount of lactoferrin at all temperature whereas IPhA retained the greatest amount of lactoferrin at all temperatures. Furthermore, IPhA reached the maximum retention state at the lowest temperature (40° C.). These results suggest that (a) CtBA retention of lactoferrin was not temperature responsive at the conditions studied (b) N-phenylacrylamide can be employed to manufacture Sepharose based temperature responsive ion exchange resins (c) the retention and release temperature for the temperature responsive on exchange resins can be altered by incorporating different monomers (NIPAAm or N-phenylacrylamide) into the polymer structure.

7a. Poly(N-Isopropylacrylamide-Co-N-Phenylacrylamide-Co-Acrylic Acid) (IPhA) Modified Sepharose New resins were synthesized using methods similar to the synthesis of ItBA. However, the type and concentrations of the monomers were varied. Briefly, Sepharose 6 FF was activated with epichlorohydrin as outlined above. The epoxy activated sepharose was then amino functionalized using aqueous ammonia by the method described herein. Free radical polymerization initiator (ACV) was immobilized onto the amino functionalized sepharose using EEDQ as the coupling agent and DMF as the solvent. Finally, polymerisation of the monomers present in the table below plus the cross-linking agent N,N-methylenebisacrylamide (MBBA) was carried out at 80° C. for 16 h in an inert atmosphere.

The various monomer compositions which were prepared are tabulated below:

| Monomers | Ratio | Abbreviation |
|---|---|---|
| NIPAAm:AA | 95:5 | (I5A) |
| NIPAAm:PhAAm:AA | 90:5:5 | (IPh5A) |
| NIPAAm:PhAAm:AA | 85:5:10 | (IPh10A) |

Figure 8:
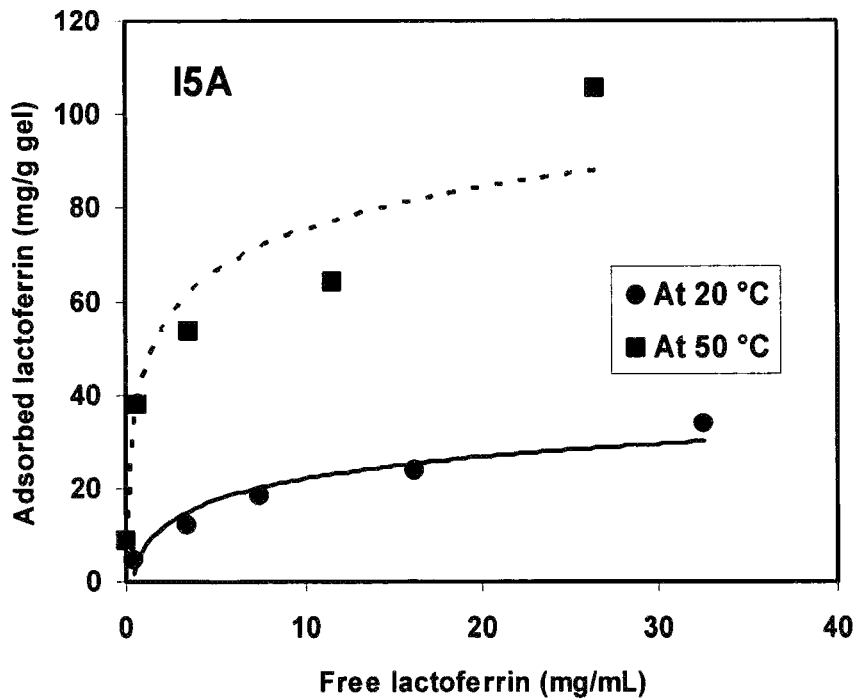
FIG. 8 shows the adsorption isotherms for lactoferrin on crosslinked agarose functionalized with poly(N-isopropylacrylamide-co-acrylic acid). The polymerization mixture contained 5% acrylic acid. Results for 20° C. and 50° C. are shown.
Figure 9:
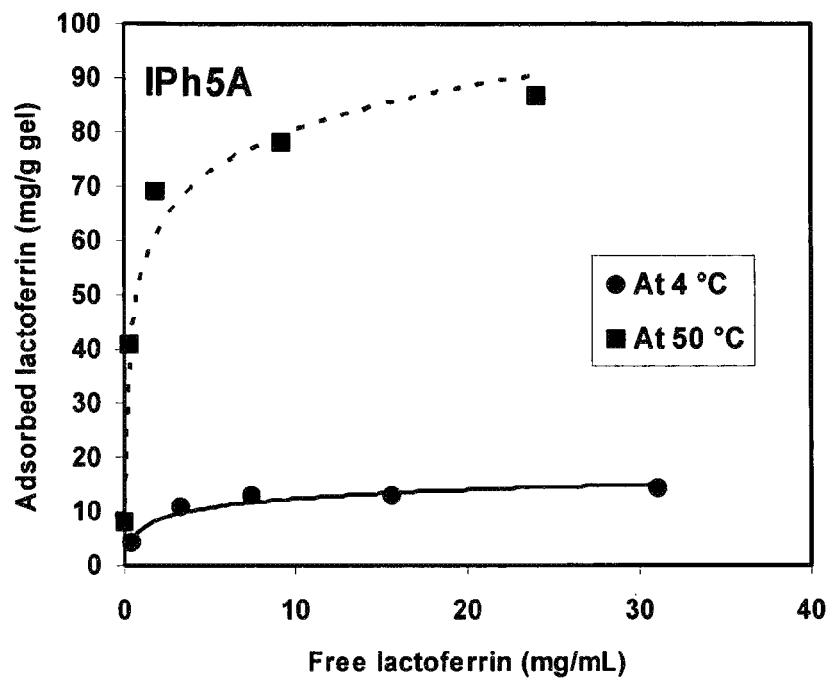
FIG. 9 shows the adsorption isotherms for lactoferrin on crosslinked agarose functionalized with poly(N-isopropylacrylamide-co-N-phenylacrylamide-co-acrylic acid). The polymerization mixture contained 5% acrylic acid. Results for 4° C. and 50° C. are shown.
Figure 10:
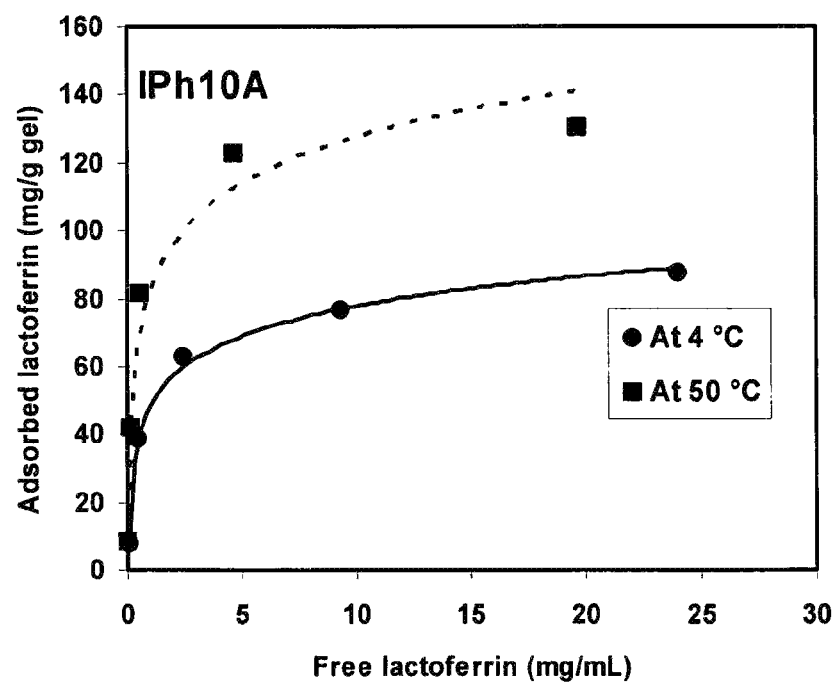
FIG. 10 shows the adsorption isotherms for lactoferrin on crosslinked agarose functionalized with poly(N-isopropylacrylamide-co-N-phenylacrylamide-co-acrylic acid). The polymerization mixture contained 10% acrylic acid. Results for 4° C. and 50° C. are shown.

Lactoferrin adsorption isotherms were obtained for the I5A at 20° C. and 50° C. (FIG. 8) and for IPh5A and IPh10A at 4° C. and 50° C. (FIGS. 9 and 10). The following method was used. Lactoferrin solutions (1 mg/mL, 5 mg/mL, 10 mg/mL, 20 mg/mL, and 40 mg/mL) were prepared in 10 mM phosphate buffer (pH 6.5) and 1 mL aliquots were mixed with 0.1 g resin samples for 35 min at the required temperature. The lactoferrin retained was calculated using the mass balance. The maximum retention capacity $B_{max}$ was then calculated from the adsorption isotherms.

For I5A there was a significant difference in the adsorption isotherms and $B_{max}$ values at 20° C. ($B_{max}$=43 mg/mL) and at 50° C. ($B_{max}$=90 mg/mL). This is demonstrated in FIG. 8.

For IPh5A, there was a significant difference in the adsorption isotherms and $B_{max}$ values at 4° C. ($B_{max}$=14 mg/mL) and at 50° C. ($B_{max}$=83 mg/mL) (FIG. 9). This was also the case for IPh10A, where there was a significant difference in the adsorption isotherms and $B_{max}$ values at 4° C. ($B_{max}$=84 mg/mL) and at 50° C. ($B_{max}$=133 mg/mL) (FIG. 10).

Increasing the acrylic acid content in the feed caused the retention capacity of the resins to increase at both low and high temperatures. However, the temperature sensitivity (retention and $B_{max}$ value difference between high and low temperatures) decreased when the acrylic acid content of the feed and thus the acrylic acid content of the copolymer attached to the resin was increased.

8. Alternative Polymer Particles for the Invention

Figure 11:
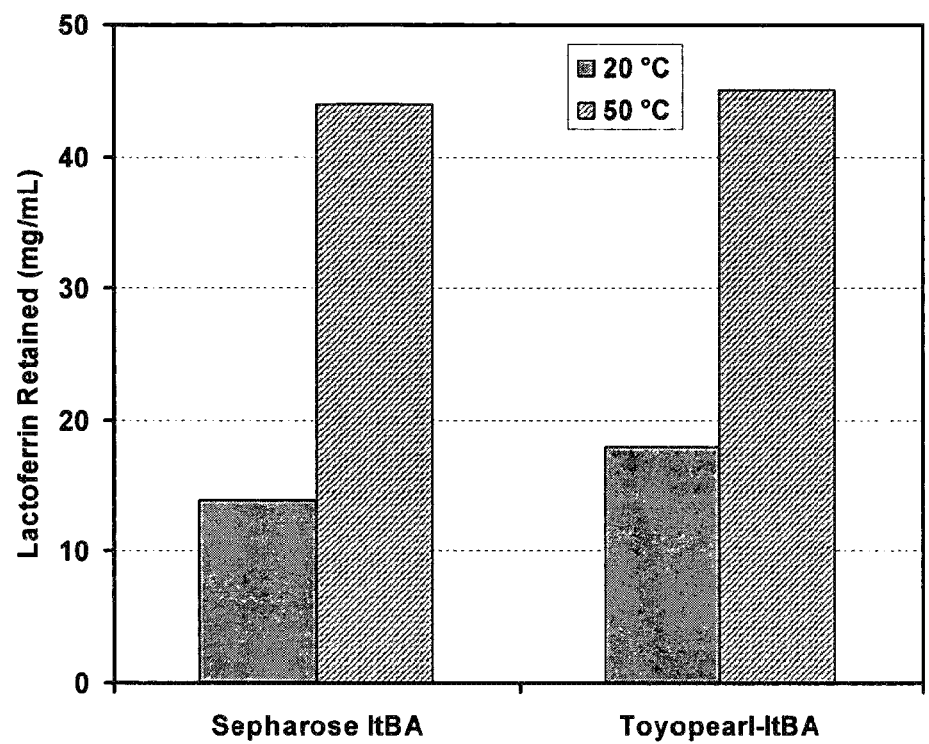
FIG. 11 shows the amount of lactoferrin retained by the ItBA and Toyopearl functionalized with poly(N-isopropylacrylamide-co-tert-butylacrylamide-co-acrylic acid (Toyopearl-ItBA) based temperature-responsive polymeric resins at 20° C. and 50° C.

The method employed to develop ItBA was adapted to develop a Toyopearl based temperature responsive ion exchange resin (Toyopearl-ItBA). ACV was immobilised onto Toyopearl® AF-Amino-650M and the polymer was developed using the same technique to that employed for ItBA (see above). The temperature responsiveness of Toyopearl-ItBA was examined using the static retention methodology employed in Example 6.1 at 20° C. and 50° C. As with ItBA, Toyopearl-ItBA retained 250% more protein at 50° C. compare to that at 20° C. (FIG. 11). These results suggest that the developed Toyopearl-based temperature responsive ion exchange resin performs in a similar manner to the Sepharose-based temperature responsive ion exchange resin.

9. Fractionation Capability of ItBA

Figure 12:
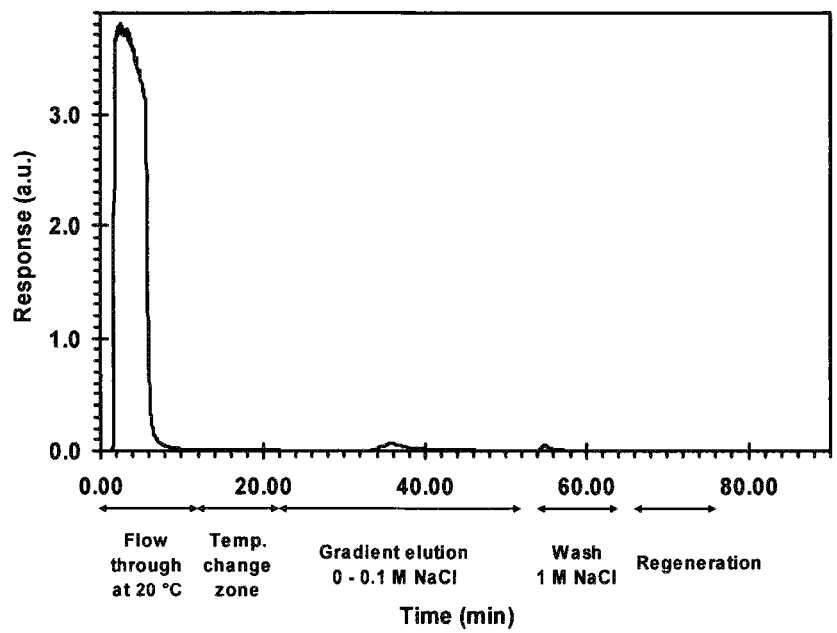
FIG. 12 is the chromatogram produced when a mixture of α-lactalbumin (12 mg), β-lactoglobulin (13 mg) and lactoferrin (24 mg) was loaded onto a column packed with ItBA with 10 mM phosphate buffer mobile phase at 20° C. for 12 min (0-12 min), followed by elution at 20° C. for 10 min (12-22 min), followed by application of a NaCl gradient from 0 M to 0.1 M over 30 min (22-52 min), and 1M NaCl for 14 min (52-66 min).
Figure 13:
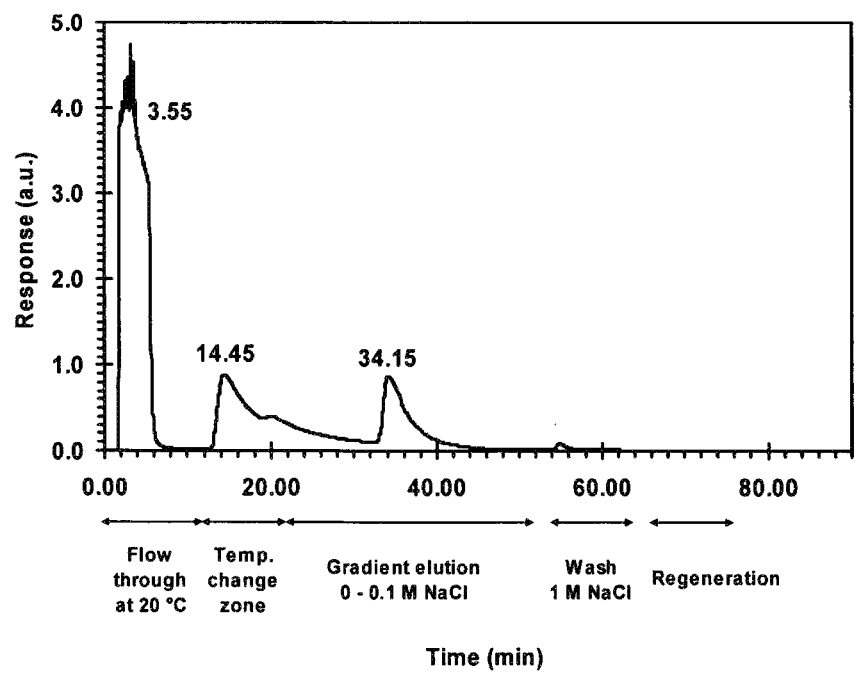
FIG. 13 is the chromatogram obtained when a mixture of α-lactalbumin (12 mg), β-lactoglobulin (13 mg) and lactoferrin (24 mg) was loaded onto a column packed with ItBA with 10 mM phosphate buffer mobile phase at 50° C. for 12 min (0-12 min), followed by elution at 20° C. for 10 min (12-22 min), followed by application of an NaCl gradient from 0 M to 0.1 M over 30 min (22-52 min), and 1M NaCl for 14 min (52-66 min).

The fractionation capability of the ItBA was examined using a model dairy whey protein solution (a mixture of α-lactalbumin (13 mg/mL), β-lactoglobulin (15 mg/mL) and lactoferrin (27 mg/mL). The method employed for the study was similar to that employed in Example 6.3. The chromatograms in FIGS. 12 and 13 show the retention and elution profiles of the model protein solution. When the model protein solution was loaded onto the column at 20°

C., the majority of the proteins were not retained and eluted from the column in the flow through fraction. However, when the model protein solution was loaded onto the column at 50° C., 50% of the lactoferrin was retained by the resin, whilst none of the α-lactalbumin and β-lactoglobulin was retained. Instead, the α-lactalbumin and β-lactoglobulin were eluted from the column the in flow-through fraction. The majority (52%) of the retained lactoferrin was eluted by reducing the mobile phase and column temperature from 50° C. to 20° C. Most of the remaining (44%) retained lactoferrin was eluted from the column with 0.1 M NaCl at 20° C. (see Tables 2 & 3). These results indicate that ItBA retains minimal cationic and anionic proteins at 20° C., and that ItBA is able to selectively retain cationic proteins (e.g. lactoferrin) at 50° C. and then release the majority of the retained cationic proteins with a temperature change (e.g. decrease to 20° C.) and salt.

TABLE 2

Amount of each protein in each eluted fraction as a percentage of the total amount of each protein loaded onto the ItBA column at 20° C. followed by elution at 20° C. and then a NaCl gradient from 0M to 1M.

| Time | Flow through 0-12 min | Temperature change 12-22 min | 0-0.1M NaCl 22-52 min | 0.1-1M NaCl 52-66 min | Re-equilibration 66-76 min |
|---|---|---|---|---|---|
| α-lactalbumin | 100 | 0 | 0 | 0 | 0 |
| lactoferrin | 99 | 0 | 1 | 0 | 0 |
| β-lactoglobulin | 100 | 0 | 0 | 0 | 0 |

TABLE 3

Amount of each protein in each eluted fraction as a percentage of the total amount of each protein loaded onto the ItBA column at 50° C. followed by elution at 20° C. and then a NaCl gradient from 0M to 1M.

| Time | Flow through 0-12 min | Temperature change 12-22 min | 0-0.1M NaCl 22-52 min | 0.1-1M NaCl 52-66 min | Re-equilibration 66-76 min |
|---|---|---|---|---|---|
| α-lactalbumin | 100 | 0 | 0 | 0 | 0 |
| lactoferrin | 48 | 25 | 21 | 2 | 0 |
| β-lactoglobulin | 100 | 3 | 0 | 0 | 0 |

10. Retention of Cytochrome C

Figure 14:
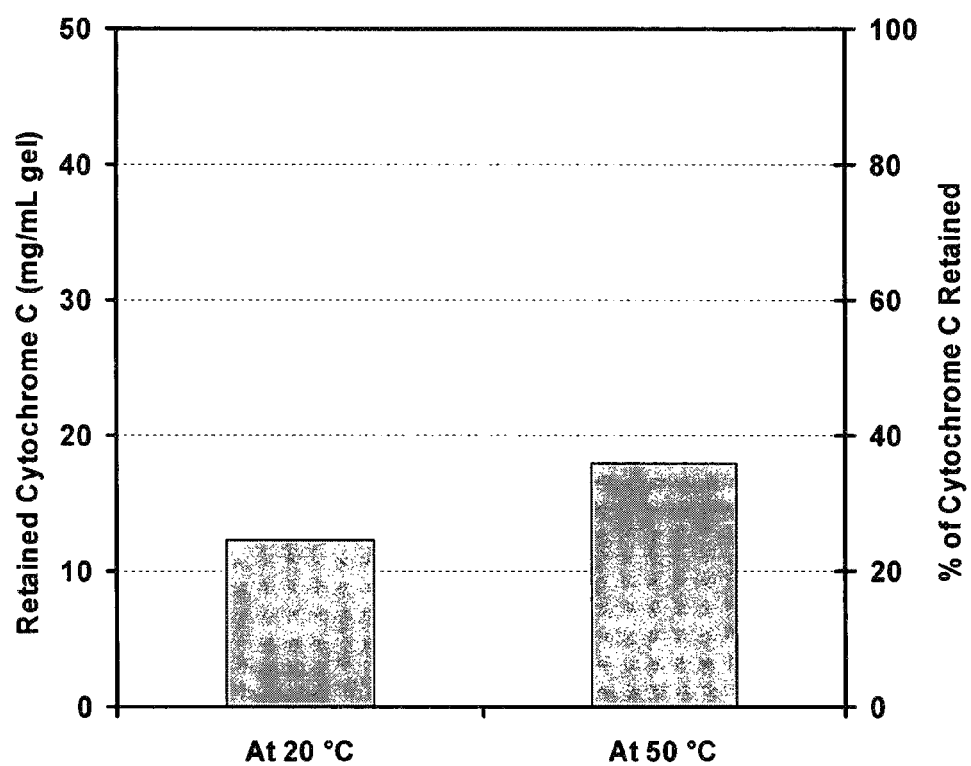
FIG. 14 shows the amount of Cytochrome C retained by the ItBA at 20° C. and 50° C., respectively.

To investigate the retention profile of other basic proteins by ItBA at 20° C. and 50° C., static retention experiments were conducted using Cytochrome C (pI: 10-10.5). ItBA (0.1 g) was mixed with a Cytochrome C solution (1 mL of 5 mg/mL) for 1 h at temperatures of 20° C. and 50° C. The resin was avowed to settle and the amount of unretained protein was determined by measuring the absorbance of the supernatant at 280 nm, which in turn gave the amount of protein retained by the resins. It was found that ItBA retained 50% more Cytochrome C at 50° C. compared to that at 20° C. (FIG. 14).

11. Studies on Protein Retention and Release from ItBA

The dynamic lactoferrin retention characteristics of the ItBA were further examined using a pure lactoferrin solution (0.9 to 45 mg/mL), a fresh whey solution containing whey proteins and lactoferrin (0.2 to 21.8 mg/mL) and a concentrated whey solution containing concentrated whey proteins (approximately a 10 fold concentrate) and lactoferrin (0.6 to 22.2 mg/mL). The method employed was similar to that employed in Example 6.3, however, contacting was only undertaken at 50° C. and release was undertaken with 0.1 M NaCl at 20° C.

Figure 15:
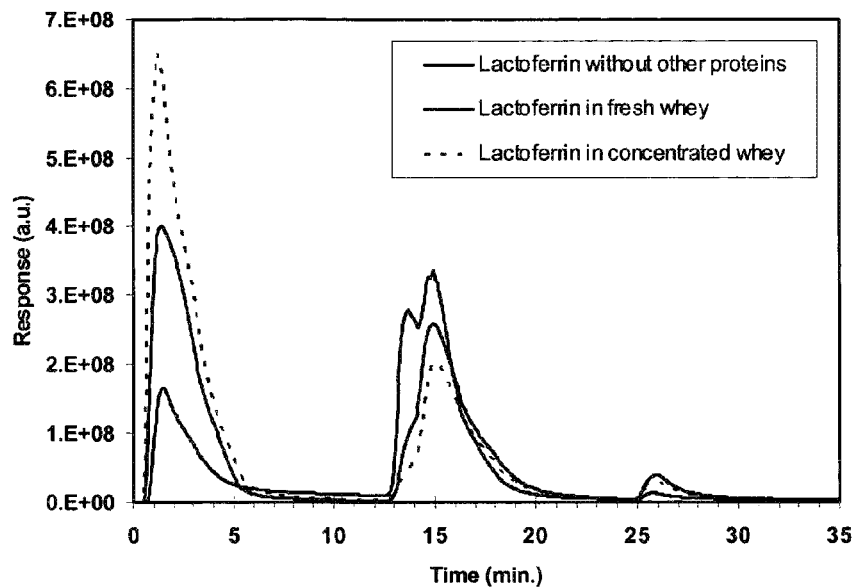
FIG. 15 shows the chromatograms obtained when similar amounts of (i) lactoferrin without other proteins, (ii) lactoferrin in a fresh whey solution, and (iii) lactoferrin in a concentrated whey solution (approximately 10 fold) were loaded dynamically and eluted from ItBA. Sample solutions (1 mL) were loaded onto a column packed with 1.7 mL of ItBA in 10 mM phosphate buffer mobile phase at 50° C. for 12 min (0-12 min), followed by elution with 0.1M NaCl at 20° C. for 10 min (13-23 min), and 1M NaCl for 10 min (25-35 min).
Figure 16:
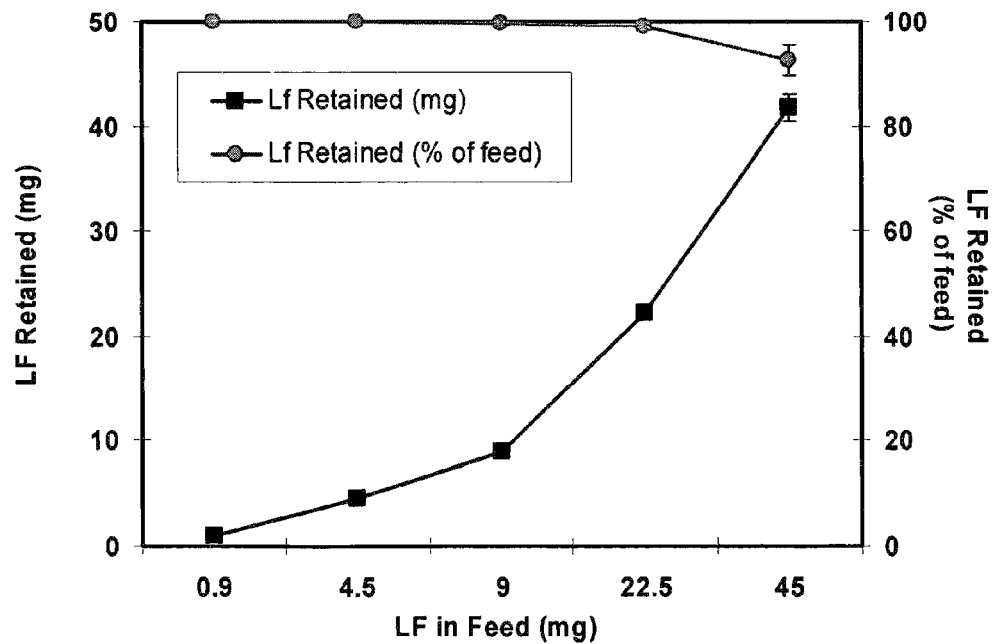
FIG. 16 shows the amount and percentage of lactoferrin retained from a solution containing only lactoferrin at different concentrations. The lactoferrin was loaded onto a column packed with 1.7 of ItBA in 10 mM phosphate buffer mobile phase at 50° C. for 12 min (0-12 min), followed by elution with 0.1M NaCl at 20° C. for 10 min (13-23 min), and 1M NaCl for 10 min (25-35 min).
Figure 17:
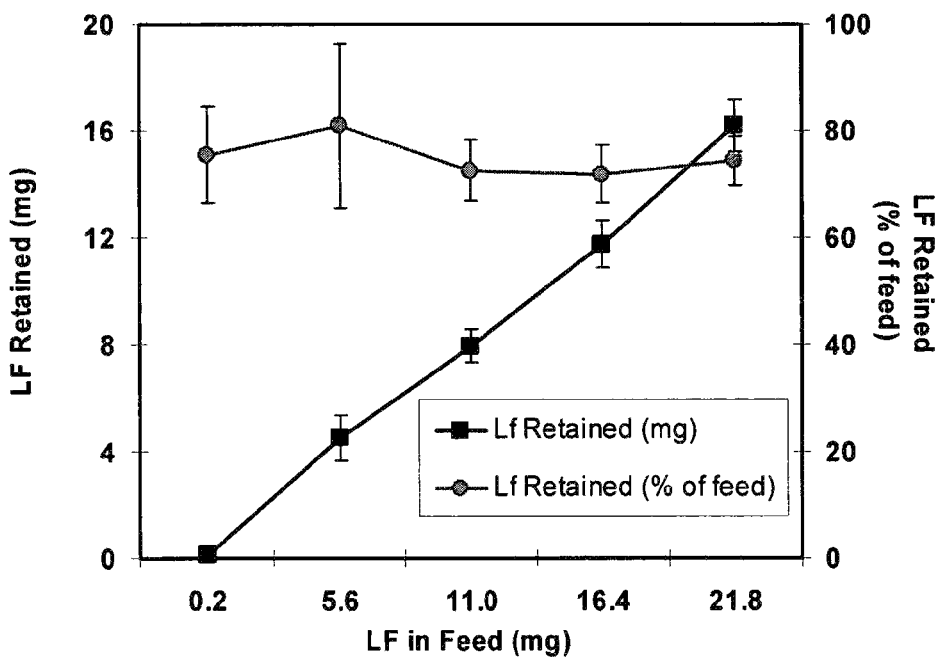
FIG. 17 shows the amount and percentage of lactoferrin retained from a fresh rennet whey solution containing lactoferrin at different concentrations. The whey was loaded onto a column packed with 1.7 mL of ItBA in 10 mM phosphate buffer mobile phase at 50° C. for 12 min (0-12 min), followed by elution with 0.1M NaCl at 20° C. for 10 min ((13-23 min), and 1M NaCl for 10 min (25-35 min).
Figure 18:
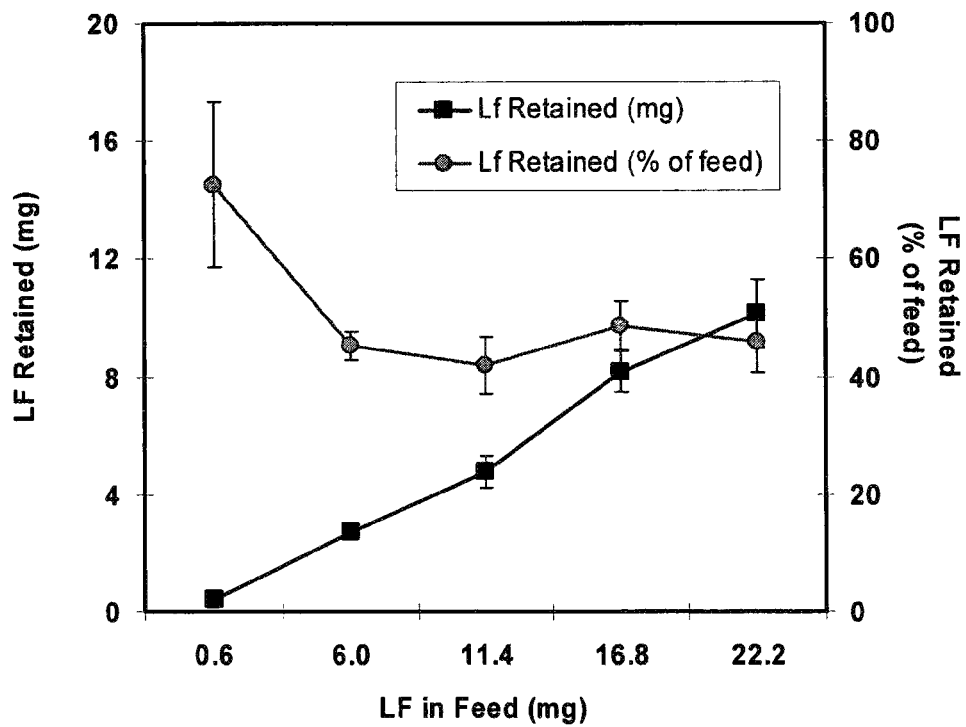
FIG. 18 shows the amount and percentage of lactoferrin retained from a real concentrated rennet whey solution containing lactoferrin at different concentrations. The concentrated whey was loaded onto a column packed with 1.7 mL of ItBA with 10 mM phosphate buffer mobile phase at 50° C. for 12 min (0-12 min), followed by elution with 0.1M NaCl at 20° C. for 10 min (13-23 min), and 1M NaCl for 10 min (25-35 min).

The chromatograms in FIG. 15 show the retention and elution profiles of the protein solutions examined. It is evident from these chromatograms that lactoferrin is retained by ItBA and can be released by the ItBA when present alone, in fresh whey or in concentrated whey. When 0.9 to 45 mg of lactoferrin was loaded onto the column without other proteins present, greater than 95% of the loaded lactoferrin was retained (FIG. 16). The percentage of lactoferrin retained did not plateau, indicating that the resin had not reached full retention capacity (FIG. 16). When 0.2 to 21.8 mg of lactoferrin was loaded onto the column in the presence of whey proteins (at their normal concentration), greater than 70% of the loaded lactoferrin was retained (FIG. 17). There was also a very linear relationship between the amount of lactoferrin in the feed and the amount of lactoferrin retained, again indicating that the resin had not reached full retention capacity (FIG. 17). When 0.6 to 22.2 mg of lactoferrin was loaded onto the column in the presence of concentrated whey proteins (concentrated approximately 10 fold), approximately 50% of the loaded lactoferrin was retained (FIG. 18). A linear relationship between the amount of lactoferrin in the feed and the amount of lactoferrin retained was also observed when using concentrated whey (FIG. 18).

These results indicate that ItBA retains lactoferrin alone and in the presence of whey proteins at their normal concentration and when concentrated approximately 10 fold.

Finally, it will be appreciated that various modifications and variations of the methods and compositions of the invention described herein will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are apparent to those skilled in the art are intended to be within the scope of the present invention.

The claims defining the invention are as follows:

1. Crosslinked hydroxylic polymer particles functionalized with temperature-responsive copolymer, wherein the temperature-responsive copolymer includes:
   a. N-isopropylacrylamide monomer units providing temperature-responsive properties to the copolymer;
   b. N-phenylacrylamide monomer units; and
   c. acrylic acid monomer units providing ionizable chemical groups to the copolymer, the temperature responsive copolymer is propagated on the hydroxylic polymer particles, and wherein the temperature responsive copolymer includes N-isopropylacrylamide units, N-phenylacrylamide units and acrylic acid units in a ratio of from 84:8:8 to 96:2:2.

2. Crosslinked hydroxylic polymer particles according to claim 1, wherein the crosslinked hydroxylic polymer is selected from the group consisting of crosslinked agarose, crosslinked cellulose, hydroxy-functional crosslinked vinyl polymer, hydroxy-functional crosslinked acrylic polymer and hydroxy-functional crosslinked methacrylic polymer.

3. Crosslinked hydroxylic polymer particles according to claim 1, wherein the crosslinked hydroxylic polymer is crosslinked agarose.

4. A method for preparing the crosslinked hydroxylic polymer particles according to claim 1, the method comprising:

a. providing initial crosslinked hydroxylic polymer particles;
b. chemically modifying the crosslinked hydroxylic polymer particles to provide crosslinked hydroxylic polymer particles having functional groups capable of initiating polymerization;
c. contacting the crosslinked hydroxylic polymer particles having functional groups capable of initiating polymerization with a monomer solution including at least one monomer capable of providing temperature-responsive properties to the copolymer and at least one monomer capable of providing ionizable chemical groups to the copolymer, wherein said contacting initiates polymerization of the monomers; and
d. isolating crosslinked hydroxylic polymer particles functionalized with temperature-responsive copolymer having a proportion of ionizable chemical groups.

5. The method according to claim 4, wherein the step of chemically modifying the crosslinked hydroxylic polymer particles to provide crosslinked hydroxylic polymer particles having functional groups capable of initiating polymerization includes the steps of
   a. Functionalising the crosslinked hydroxylic polymer particles with at least one epoxide group;
   b. Reacting the epoxide group with ammonia to provide crosslinked hydroxylic polymer particles functionalized with amine groups;
   c. Reacting the amine groups with a polymerization initiator having at least one carboxylic acid group.

6. The method according to claim 5, wherein the step of functionalizing the crosslinked hydroxylic polymer particles with at least one epoxide group includes reacting hydroxylic polymer particles with epichlorohydrin in the presence of sodium hydroxide and sodium borohydride.

7. The method according to claim 5, wherein the polymerization initiator having at least one carboxylic acid group is 4,4'azobis(4-cyanovaleric acid).

* * * * *